(12) United States Patent
Kuwano et al.

(10) Patent No.: US 8,728,396 B2
(45) Date of Patent: May 20, 2014

(54) SAMPLE ANALYZER AND SAMPLE TRANSPORTING METHOD

(75) Inventors: Keisuke Kuwano, Kobe (JP); Daigo Fukuma, Kobe (JP)

(73) Assignee: Sysmex Corporation, Kobe (JP)

( * ) Notice: Subject to any disclaimer, the term of this patent is extended or adjusted under 35 U.S.C. 154(b) by 339 days.

(21) Appl. No.: 13/044,100

(22) Filed: Mar. 9, 2011

(65) Prior Publication Data

US 2011/0223580 A1    Sep. 15, 2011

(30) Foreign Application Priority Data

Mar. 10, 2010  (JP) .................................. 2010-052836

(51) Int. Cl.
| | |
|---|---|
| *G01N 21/00* | (2006.01) |
| *G01N 31/00* | (2006.01) |
| *G01N 33/00* | (2006.01) |
| *G01N 35/02* | (2006.01) |
| *G01N 35/00* | (2006.01) |

(52) U.S. Cl.
USPC ................... 422/67; 422/62; 422/63; 422/65; 436/43; 436/44; 436/47; 436/48

(58) Field of Classification Search
None
See application file for complete search history.

(56) References Cited

U.S. PATENT DOCUMENTS

| | | | | |
|---|---|---|---|---|
| 5,380,488 | A * | 1/1995 | Wakatake | ...................... 422/65 |
| 6,261,521 | B1 * | 7/2001 | Mimura et al. | ................. 422/67 |
| 6,723,288 | B2 * | 4/2004 | Devlin et al. | .................. 422/65 |
| 7,101,715 | B2 * | 9/2006 | Devlin et al. | .................. 436/43 |
| 2009/0227033 | A1 | 9/2009 | Hamada et al. | |

* cited by examiner

*Primary Examiner* — Jill Warden
*Assistant Examiner* — Julie Tavares
(74) *Attorney, Agent, or Firm* — Brinks Gilson & Lione

(57) ABSTRACT

The present invention is a sample analyzer including: a first and a second measurement unit configured to measure a sample accommodated in a sample container; a rack transport unit configured to transport each of a plurality of sample containers held in a sample rack to either the first or the second measurement unit; and a controller configured to acquire a measurement item information indicating a measurement item of each of samples accommodated in the plurality of sample containers held in the sample rack, determine a sample container to be a transport object and a measurement unit to be a transport destination of the sample container based on the acquired plurality of measurement item information, and control the rack transport unit to transport the sample container determined as the transport object to the measurement unit determined as the transport destination.

17 Claims, 14 Drawing Sheets

| PRIORITY | COMMAND |
|---|---|
| 1 | RACK DISCHARGING COMMAND |
| 2 | RACK SENDING COMMAND |
| 3 | RACK ID READING COMMAND |
| 4 | SAMPLE CONTAINER RETRIEVING COMMAND |
| 5 | SAMPLE CONTAINER RETURNING COMMAND |
| 6 | SAMPLE INFORMATION ASSIGNING COMMAND |

SAMPLE ANALYZER AND SAMPLE TRANSPORTING METHOD

RELATED APPLICATIONS

This application claims priority under 35 U.S.C. §119 to Japanese Patent Application No. 2010-052836 filed on Mar. 10, 2010, the entire content of which is hereby incorporated by reference.

BACKGROUND OF THE INVENTION

1. Field of the Invention

The present invention relates to a sample analyzer including a transportation unit for transporting a plurality of sample containers accommodating samples and a measurement unit for measuring the samples accommodated in the sample containers, and a sample transporting method by the sample analyzer.

2. Description of the Related Art

A sample analyzer including a plurality of measurement devices for measuring samples such as blood or urine, and a sample transporting device for distributing a plurality of sample containers to the plurality of measurement devices is conventionally known.

U.S. Patent Publication No. 2009/0227033 discloses a sample analyzer including a first measurement unit, a second measurement unit for measuring samples for other measurement items in addition to measurement items measured by the first measurement unit, and a sample transporting device for transporting a rack accommodating a plurality of sample containers to the first measurement unit and the second measurement unit. In such sample analyzer, when an instruction to start measurement is made by the user, the sample transporting device transports the plurality of sample containers accommodated in the rack, sequentially one by one from the sample container positioned at the head of the rack, to a measurement unit in a state capable of measuring measurement items of the sample in the sample container. The measurement is then carried out sequentially from the sample in the sample container positioned on the head side of the rack.

However, in some racks, a sample (first sample) whose measurement order includes only the measurement item that can be measured in both first and second measurement units and a sample (second sample) whose measurement order includes the measurement item that can be measured only in the second measurement unit coexist. For instance, sample containers from the head to the mth sample container of n sample containers lined in the rack (m is a plural, and n−m≥2) may accommodate the first sample, and (m+1)th to nth sample containers may accommodate the second sample. In such a case, as in the sample transporting device disclosed in U.S. Patent Publication No. 2009/0227033, if the n sample containers accommodated in the rack are transported to the first and second measurement units sequentially from the sample container positioned at the head side of the rack, the sample containers from the head to the mth sample containers are distributed sequentially to the first and second measurement units and measured, and then the (m+1)th to nth sample containers are transported to the second measurement unit sequentially and measured. While the second samples in the (m+1)th to nth sample containers are continuously measured by the second measurement unit, the sample containers are not transported to the first measurement unit. Therefore, in such a case, the first measurement unit cannot be effectively used, and the processing efficiency of the entire sample analyzer may become lower.

SUMMARY OF THE INVENTION

The scope of the present invention is defined solely by the appended claims, and is not affected to any degree by the statements within this summary.

A first aspect of the present invention is a sample analyzer comprising: a first measurement unit configured to measure a sample accommodated in a sample container; a second measurement unit configured to measure a sample accommodated in a sample container; a rack transport unit configured to transport each of a plurality of sample containers held in a sample rack to either the first or the second measurement unit; and a controller configured to acquire a measurement item information indicating a measurement item of each of samples accommodated in the plurality of sample containers held in the sample rack, determine a sample container to be a transport object and a measurement unit to be a transport destination of the sample container based on the acquired plurality of measurement item information, and control the rack transport unit to transport the sample container determined as the transport object to the measurement unit determined as the transport destination.

A second aspect of the present invention is a sample transporting method for transporting each of a plurality of sample containers held in a sample rack to a first measurement unit and a second measurement unit by a rack transport unit; the method comprising: a first step of acquiring a measurement item information indicating a measurement item of each of samples accommodated in the plurality of sample containers held in the sample rack; a second step of determining a sample container to be a transport object from the plurality of sample containers based on the plurality of measurement item information acquired in the first step, and determining a measurement unit to be a transport destination of the sample container determined as the transporting object from the first and second measurement units; and a third step of transporting the sample container determined as the transport object to the measurement unit determined as the transport destination by the rack transport unit.

DETAILED DESCRIPTION OF THE PREFERRED EMBODIMENTS

The preferred embodiment of the present invention will now be described with reference to the drawings.

[Configuration of Sample Analyzer]

Figure 1A:
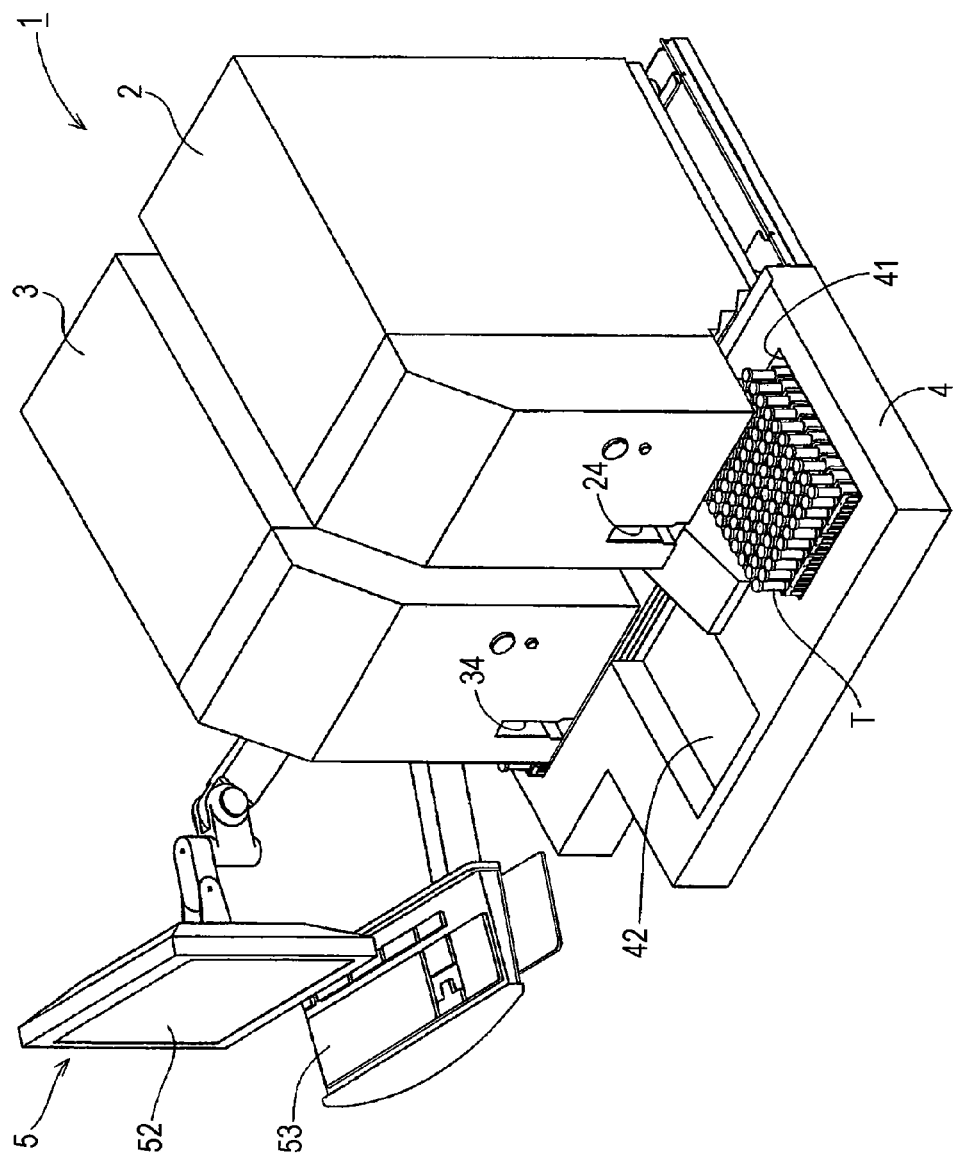
FIG. 1A is a perspective view showing an overall configuration of a sample analyzer according to the embodiment.
Figure 1B:
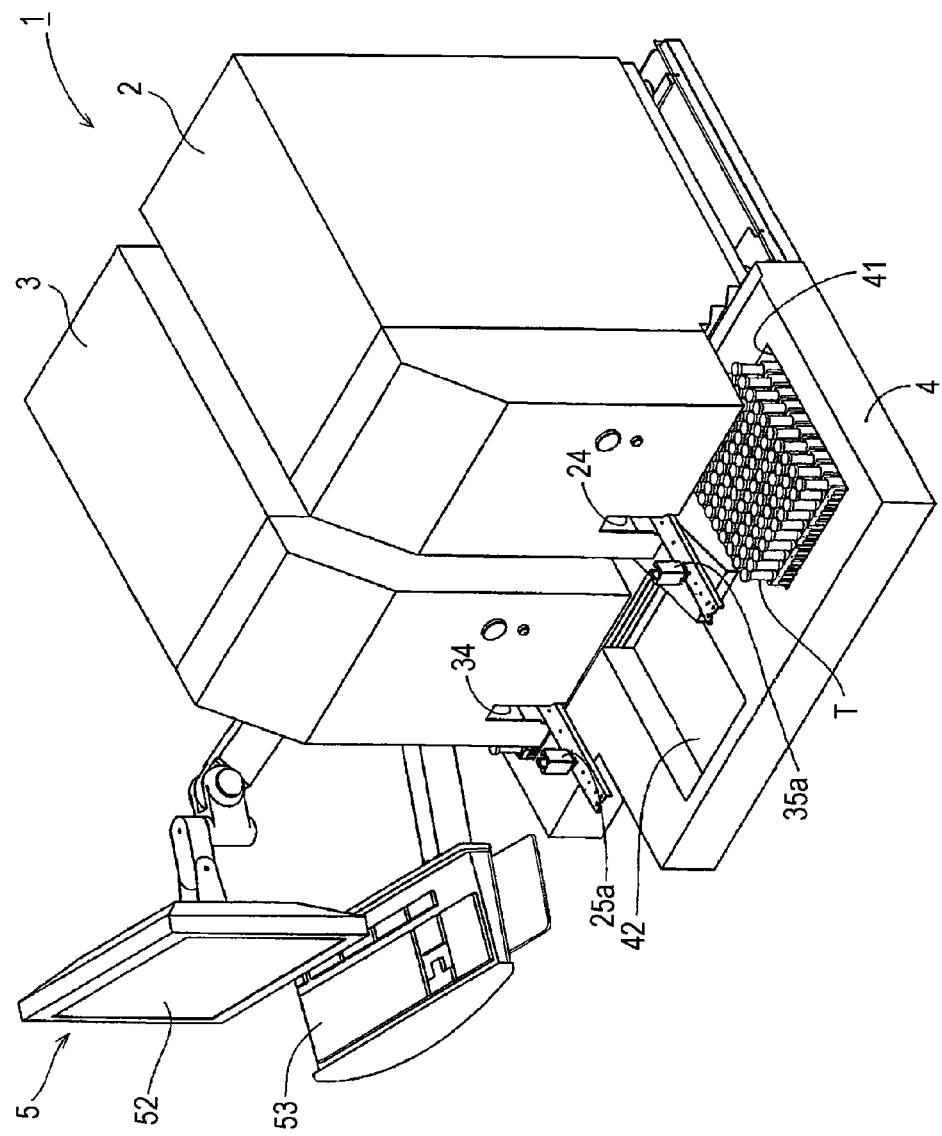
FIG. 1B is a perspective view showing an overall configuration of the sample analyzer according to the embodiment.

FIG. 1A and FIG. 1B are perspective views showing the overall configuration of a sample analyzer according to the present embodiment. A sample analyzer 1 according to the present embodiment is a multi-item blood cells analyzer for classifying the blood cells contained in the blood sample into white blood cells, red blood cells, blood platelets, and the like, and counting each blood cell. As shown in FIG. 1A and FIG. 1B, the sample analyzer 1 includes a first measurement unit 2, a second measurement unit 3, a sample transport unit 4 arranged on the front surface side of the first measurement unit 2 and the second measurement unit 3, and an information processing unit 5 capable of controlling the first measurement unit 2, the second measurement unit 3, and the sample transport unit 4.

Figure 2:
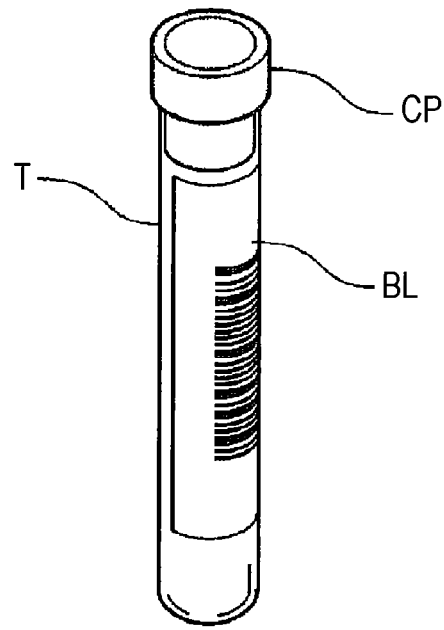
FIG. 2 is a perspective view showing an outer appearance of a sample container.
Figure 3:
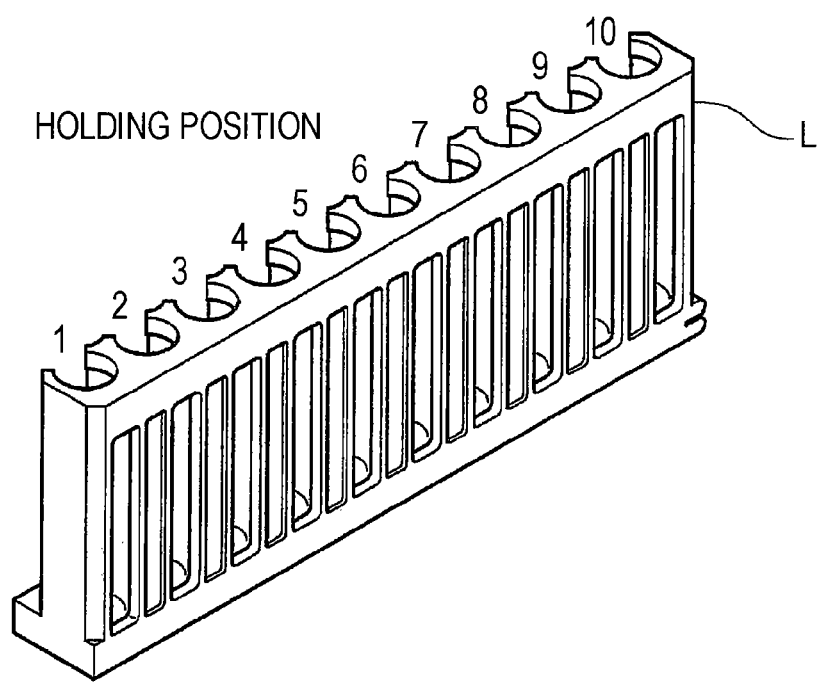
FIG. 3 is a perspective view showing an outer appearance of a sample rack.

FIG. 2 is a perspective view showing an outer appearance of a sample container for accommodating the samples, and FIG. 3 is a perspective view showing an outer appearance of a sample rack for holding a plurality of sample containers. As shown in FIG. 2, a sample container T has a tubular shape with the upper end opened. The blood sample collected from a patient is accommodated inside, and the opening at the upper end is sealed by a lid CP. The sample container T is configured by glass or synthetic resin having translucency, so that the blood sample inside is visible. A barcode label BL is attached to the side surface of the sample container T. The barcode label BL is printed with a barcode indicating a sample ID. Referring to FIG. 3, the sample rack L can hold ten sample containers T in a line. Each sample container T is held in a vertical state (standing state) in the sample rack L. A barcode label printed with a barcode indicating a rack ID is attached to the side surface of the sample rack L (not shown).

<Configuration of Measurement Unit>

Figure 4:
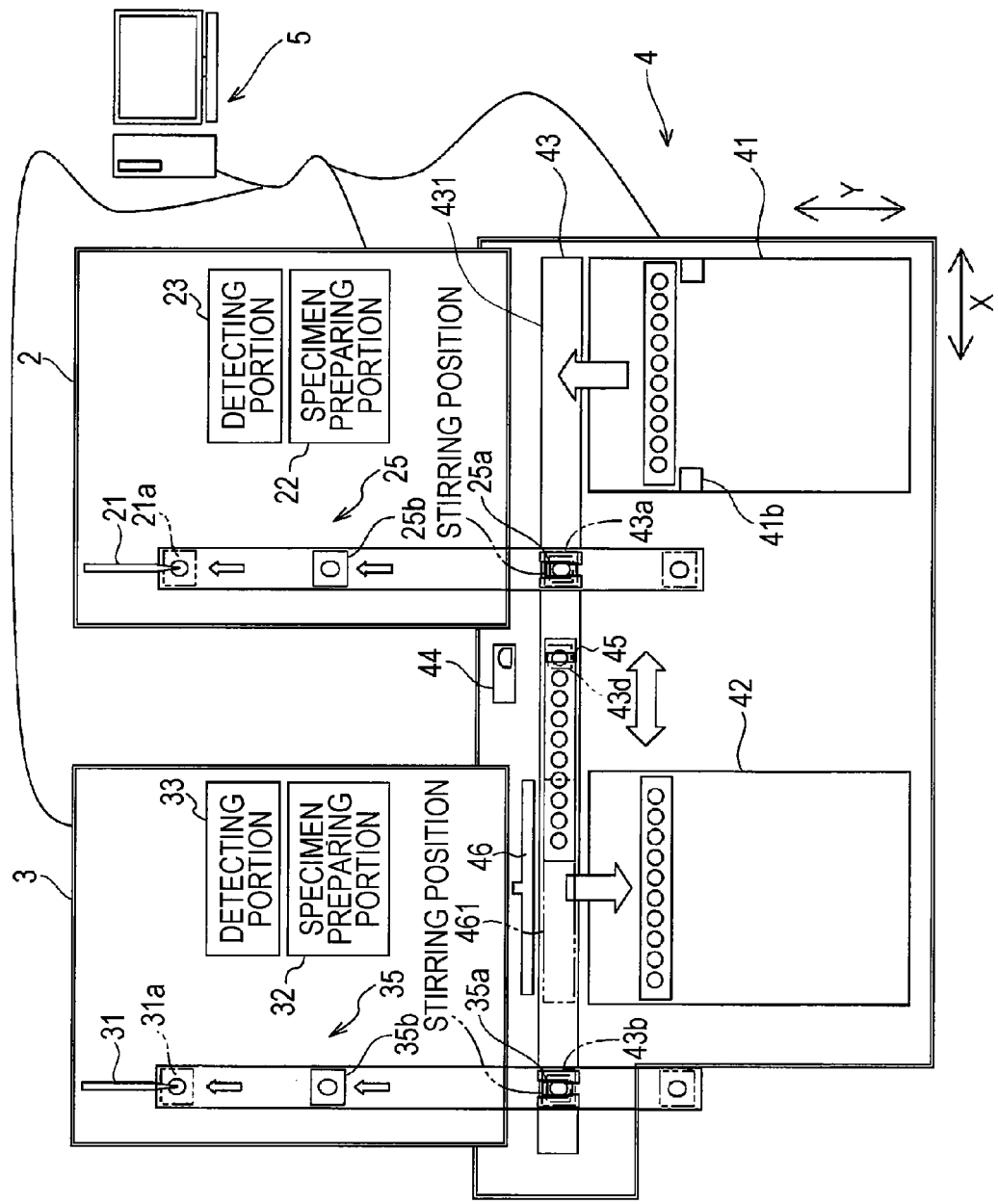
FIG. 4 is a schematic view showing the configuration of a sample analyzer according to the embodiment.

FIG. 4 is a schematic view showing the configuration of a sample analyzer 1 according to the present embodiment. The first measurement unit 2 is arranged on an upstream side (pre-analysis rack holding portion 41 side) in the transporting direction (X direction shown in FIG. 4) of the sample of the sample transport unit 4, and the second measurement unit 3 is arranged on a downstream side (post-analysis rack holding portion 42 side) in the transporting direction. As shown in FIG. 4, the first measurement unit 2 includes a sample aspirating portion 21 for aspirating the blood or the sample from the sample container (blood collecting tube) T, a specimen preparing portion 22 for preparing a measurement specimen used in the measurement of a blood component such as blood cells from the blood aspirated by the sample aspirating portion 21, and a detecting portion 23 for detecting (measuring) the blood cells from the measurement specimen prepared by the specimen preparing portion 22. The first measurement unit 2 also includes a take-in port 24 for taking in the sample container T accommodated in the sample rack L transported by a rack transporting portion 43 of the sample transport unit 4 into the first measurement unit 2 (see FIG. 1A and FIG. 1B), and a sample container transporting portion 25 for taking in the sample container T into the first measurement unit 2 from the sample rack L and transporting the sample container T to an aspirating position by the sample aspirating portion 21.

As shown in FIG. 4, an aspirating tube (not shown) is arranged at the distal end of the sample aspirating portion 21. The sample aspirating portion 21 is movable in the vertical direction, and is configured to move downward so that the aspirating tube penetrates through the lid CP of the sample container T transported to the aspirating position and the blood inside is aspirated.

The specimen preparing portion 22 includes a plurality of reaction chambers (not shown). The specimen preparing portion 22 is connected to a reagent container (not shown), and can supply reagents such as dyeing reagent, hemolytic agent, and diluting solution to the reaction chamber. The specimen preparing portion 22 is also connected to the aspirating tube of the sample aspirating portion 21, so that the blood sample aspirated by the aspirating tube can be supplied to the reaction chamber. The relevant specimen preparing portion 22 mixes and stirs the sample and the reagent in the reaction chamber, and prepares a specimen for measurement (measurement specimen) by the detecting portion 23.

The detecting portion 23 can carry out the RBC (red blood cell) detection and the PLT (blood platelet) detection through the sheath flow DC detection method. In the detection of the RBC and the PLT through the sheath flow DC detection method, the measurement specimen in which the sample and the diluting solution are mixed is measured, and the measurement data obtained therefrom are subjected to an analyzing process by the information processing unit 5 to acquire the numerical value data of the RBC and the PLT. The detecting portion 23 can perform the HGB (hemoglobin) detection through the SLS-hemoglobin method, and can carry out the detection of the WBC (white blood cells), NEUT (neutrophilic cells), LYMPH (lymphocyte cells), EO (acidophilic leucocytes), BASO (basophilic leucocytes), and MONO (monocytes) through the flow cytometry method using the semiconductor laser. In the detecting portion 23, the detecting methods differ between the detection of the WBC that does not involve the detection of five categories of the white blood cells, that is, NEUT, LYMPH, EO, BASO, and MONO, and the detection of the WBC that involves the five categories of the white blood cells. In the detection of the WBC that does not involve the five categories of the white blood cells, the measurement specimen in which the sample, the hemolytic agent, and the diluting solution are mixed is measured, and the measurement data obtained therefrom are subjected to the analyzing process by the information processing unit 5 to acquire the numerical value data of the WBC. In the detection of the WBC that involves the five categories of the white blood cells, the measurement specimen in which the sample, the dyeing reagent for the five categories of the white blood cells, the hemolytic agent, and the diluting solution are mixed is measured, and the measurement data obtained therefrom are subjected to the analyzing process by the information processing unit 5 to acquire the numerical value data of the NEUT, LYMPH, EO, BASO, MONO, and WBC.

The WBC, RBC, PLT, and HGB are contained in the measurement item called the CBC item, and the WBC, RBC, PLT, HGB, NEUT, LYMPH, EO, BASO, and MONO are contained in the measurement item called the CBC+DIFF item. In the present embodiment, both the first measurement unit 2 and the second measurement unit 3 are configured to be able to measure the CBC+DIFF item.

The detecting portion 23 includes a flow cell (not shown), and is configured to generate a solution flow in the flow cell by sending the measurement specimen to the flow cell, irradiate the blood cells contained in the solution flow passing through the flow cell with a semiconductor laser light, and detect the forward scattered light, the lateral scattered light, and the lateral fluorescence.

The light scattering is a phenomenon that occurs when particles such as blood cells exist as an obstruction in the advancing direction of the light and the light changes its advancing direction. The information regarding the size and the material of the particles can be obtained by detecting the scattered light. In particular, the information regarding the size of the particle (blood cell) can be obtained from the forward scattered light. The information on the interior of the particle can be obtained from the lateral scattered light. When the blood cell particles are irradiated with the laser light, the lateral scattered light intensity depends on the complexity of the interior of the cell (shape of core, size, density, amount of granule). Therefore, the measurement on the categories of the white blood cells and other measurements can be carried out by using the characteristics of the lateral scattered light intensity.

When a fluorescent substance such as dyed blood cell is irradiated with light, a light having a longer wavelength than the wavelength of the irradiated light is generated. The intensity of the fluorescent light becomes stronger if satisfactorily dyed, and the information regarding the degree of dyeing of the blood cells can be obtained by measuring the intensity of the fluorescent light. Therefore, the measurement on the categories of the white blood cells and other measurements can be carried out by the difference in the (lateral) fluorescent light intensity.

The configuration of the sample container transporting unit 25 will now be described. The sample container transporting portion 25 includes a hand portion 25a capable of gripping the sample container T. The hand portion 25a includes a pair of gripping members arranged facing each other, and such gripping members can be moved closer or moved away to and from each other. The sample container T can be gripped by bringing the grip members closer while sandwiching the sample container T. The sample container transporting portion 25 can move the hand portion 25a in the up and down direction and the front and back direction (Y direction), and can also oscillate the hand portion 25a. Thus, the sample container T accommodated in the sample rack L and positioned at a first sample supply position 43a can be gripped by the hand portion 25a, and the hand portion 25a can be moved upward in such state to take out the sample container T from the sample rack L, and the sample in the sample container T can be stirred by oscillating the hand portion 25a.

The sample container transporting portion 25 also includes a sample container setting portion 25b with a hole to which the sample container T can be inserted. The sample container T gripped by the above mentioned hand portion 25a is moved after stirring is completed, and the gripped sample container T is inserted to the hole of the sample container setting portion 25b. Thereafter, the gripping members are moved apart to release the sample container T from the hand portion 25a, and the sample container T is set in the sample container setting portion 25b. The relevant sample container setting portion 25b is horizontally movable in the Y direction by a power from a stepping motor (not shown).

The sample container setting portion 25b is movable to the aspirating position 21a by the sample aspirating portion 21. When the sample container setting portion 25b is moved to the aspirating position, the sample is aspirated by the sample aspirating portion 21 from the set sample container T.

The configuration of the second measurement unit 3 will now be described. The configuration of the second measurement unit 3 is the same as the configuration of the first measurement unit 2, and the second measurement unit 3 includes a sample aspirating portion 31, a specimen preparing portion 32 for preparing a measurement specimen used in the measurement of a blood component such as blood cells from the blood aspirated by the sample aspirating portion 31, and a detecting portion 33 for detecting the blood cells from the measurement specimen prepared by the specimen preparing portion 32. The second measurement unit 3 also includes a take-in port 34 for taking in the sample container T accommodated in the sample rack L transported by the rack transporting portion 43 of the sample transport unit 4 into the second measurement unit 3 (see FIG. 1A and FIG. 1B), and a sample container transporting portion 35 for taking in the sample container T into the second measurement unit 3 from the sample rack L and transporting the sample container T to an aspirating position by the sample aspirating portion 31. The configurations of the sample aspirating portion 31, the specimen preparing portion 32, the detecting portion 33, the take-in port 34, and the sample container transporting portion 35 are similar to the configurations of the sample aspirating portion 21, the specimen preparing portion 22, the detecting portion 23, the take-in port 24, and the sample container transporting portion 25, and thus the description thereof will be omitted.

Similar to the first measurement unit 2, the second measurement unit 3 can measure the sample on each measurement item of WBC, RBC, PLT, HGB, NEUT, LYMPH, EO, BASO, and MONO, which are CBC+DIFF items. The configuration of the second measurement unit 3 is similar to the configuration of the first measurement unit, and thus the description thereof will be omitted.

The second measurement unit 3 is loaded with a measurement reagent for the reticulocytes (RET) and the nucleated erythrocytes (NRBC) in addition to the measurement reagent for each measurement item of WBC, RBC, PLT, HGB, NEUT, LYMPH, EO, BASO, and MONO, which are CBC+DIFF items that can be measured by the first measurement unit 2. The measurement operation of the first measurement unit 2 is controlled by a sled corresponding to the measurement of the CBC+DIFF items contained in the process activated by the execution of a computer program 54a, to be described later, whereas the measurement operation of the second measurement unit 3 is controlled by a sled corresponding to the measurement of the measurement items of RET and NRBC in addition to the sled corresponding to the measurement of the above mentioned CBC+DIFF items. The second measurement unit 3 thus can measure the sample for the measurement items RET and NRBC in addition to the CBC+DIFF items that can be measured by the first measurement unit 2. In the second measurement unit 3, the measurement of RET is carried out by preparing a measurement specimen by mixing the reagent for RET measurement and the sample, and supplying the measurement specimen to the optical detecting section for WBC/DIFF (five categories of white blood cells) of the detecting portion 33. The measurement of NRBC is carried out by preparing a measurement specimen by mixing the reagent for NRBC measurement and the sample, and supplying the measurement specimen to the optical detecting section for WBC/DIFF (five categories of white blood cells) of the detecting portion 33.

The first measurement unit 2 and the second measurement unit 3 thus can taken in the sample container T accommodating other samples while measuring the measurement specimen prepared from one sample in the detecting portions 23, 33.

<Configuration of Sample Transport Unit>

The configuration of the sample transport unit 4 will now be described. As shown in FIG. 1A and FIG. 1B, the sample transport unit 4 is arranged on the front side of the first measurement unit 2 and the second measurement unit 3 of the sample analyzer 1. The sample transport unit 4 can transport the sample rack L to supply the sample to the first measurement unit 2 and the second measurement unit 3.

As shown in FIG. 4, the sample transport unit 4 includes a pre-analysis rack holding portion 41 for temporarily holding a plurality of sample racks L holding the sample containers T accommodating the sample before the analysis, a post-analysis rack holding portion 42 for temporarily holding the plurality of sample racks L holding the sample containers T from which the sample is aspirated by the first measurement unit 2 or the second measurement unit 3, a rack transport path 43 for linearly moving the sample rack L horizontally in the X direction as shown in the figure to supply the sample to the first measurement unit 2 or the second measurement unit 3 and transporting the sample rack L received from the pre-analysis rack holding portion 41 to the post-analysis rack holding portion 42, a barcode reading portion 44, and a sample container sensor 45 for detecting the presence of the sample container T.

The pre-analysis rack holding portion 41 is a square in plan view, the width of which is slightly greater than the width of the sample rack L. The pre-analysis rack holding portion 41 is formed to be one step lower than the peripheral surface, so that the sample rack L of before the analysis is mounted on the upper surface thereof. A rack sending portion 41b is arranged so as to be able to project out towards the inner side from both side surfaces of the pre-analysis rack holding portion 41. The rack sending portion 41b projects out to engage with the sample rack L, and is moved backward (direction of moving closer to the rack transport path 43) in such state so that the sample rack L can be moved backward. The rack sending portion 41b is configured to be drivable by a stepping motor (not shown) arranged on the lower side of the pre-analysis rack holding portion 41.

As shown in FIG. 4, the rack transport path 43 is a transport path for transporting the sample rack L transported by the pre-analysis rack holding portion 41 in the X direction. A first sample supply position 43a for supplying the sample to the first measurement unit 2 and a second sample supply position 43b for supplying the sample to the second measurement unit 3 as shown in FIG. 4 are on the rack transport path 43. The sample transport unit 4 includes a transport mechanism 431 including a belt conveyor, so that the sample rack can be transported along the rack transport path 43 by the transport mechanism 431. The sample transport unit 4 is controlled by an information processing unit 5. When the sample is transported to the first sample supply position 43a or the second sample supply position 43b, the hand portion 25a or 35a of the corresponding measurement unit grips the transported sample container T and takes out the sample container T from the sample rack L. The sample is thereby supplied to the first measurement unit 2 or the second measurement unit 3. The hand portion 25a or 35a gripping the sample container T enters into the housing of the first measurement unit 2 or the second measurement unit 3 as described above, so that the sample container T is thereby taken into the first measurement unit 2 or the second measurement unit 3. The sample transport unit 4 can transport the sample rack L on the rack transport path 43 even while the sample container T is being taken into the first measurement unit 2 or the second measurement unit 3. Therefore, while one of the first measurement unit 2 or the second measurement unit 3 is taking in the sample container T, the relevant measurement unit cannot further take in the sample container T, and hence the sample rack L is transported to the other measurement unit so that the sample container T can be taken in. Furthermore, after the aspiration of the sample from the sample container T is completed, the relevant sample container T is discharged from the first measurement unit 2 or the second measurement unit 3 and returned to the holding position of the sample rack L held before being taken in.

The barcode reading portion 44 is configured to read the barcode printed on the barcode label BL of the sample container T and the barcode printed on the barcode label attached to the sample rack L. The barcode printed on the barcode label of the sample rack L is uniquely given to each rack, and is used to manage the analysis result of the sample, and the like. A barcode reading position 43d is provided between the first sample supply position 43a and the second sample supply position 43b on the rack transport path 43, and the barcode reading portion 44 is arranged near the barcode reading position 43d. The barcode reading portion 44 thus can read the sample barcode of the sample container T positioned at the barcode reading position 43d.

The sample container sensor 45 is a contact-type sensor and includes a curtain-shaped contact piece, a light emitting element for emitting light, and a light receiving element (not shown). The sample container sensor 45 is configured such that the contact piece bends when contacting an object to be detected or the detection target, so that the light emitted from the light emitting element is reflected by the contact piece and enters the light receiving element. Thus, when the sample container T to be detected accommodated in the sample rack L passes the lower side of the sample container sensor 45, the contact piece is bent by the sample container T and the sample container T can be detected. The sample container sensor 45 is arranged at the barcode reading position 43d. The presence of the sample container T at the barcode reading position 43d thus can be detected by the sample container sensor 45.

The post-analysis rack holding portion 42, to be described later, is arranged at the end on the downstream side in the transporting direction of the rack transport path 43, and a rack sending portion 46 is arranged at the back side of the post-analysis rack holding portion 42. The rack sending portion 46 is configured to linearly move horizontally in the Y direction shown with the arrow by the drive force of the stepping motor (not shown). When the sample rack L is transported to the position 461 (hereinafter referred to as "post-analysis rack sending position") between the post-analysis rack holding portion 42 and the rack sending portion 46, the rack sending portion 46 is moved to the post-analysis rack holding portion 42 side so that the sample rack L can be pushed and moved into the post-analysis rack holding portion 42.

The post-analysis rack holding portion 42 has a square shape in plan view, the width of which is slightly greater than the width of the sample rack L. The post-analysis rack holding portion 42 is formed to be one step lower than the peripheral surface, so that the sample rack L completed with analysis is mounted on the upper surface thereof. The post-analysis rack holding portion 42 is continued to the rack transport path 43, and the sample rack L is sent from the rack transport path 43 by the rack sending portion 46, as described above.

With such configuration as described above, the sample transport unit 4 transports the sample rack L mounted on the pre-analysis rack holding portion 41 to the rack transport path 43, where the transport mechanism 431 transports the sample to the barcode reading position 43*d* along the rack transport path 43, the detection on the presence of the sample container and the reading of the sample ID are carried out, and the sample, the sample ID of which is read, is transported to the first sample supply position 43*a* or the second sample supply position 43*b* to be supplied to the first measurement unit 2 or the second measurement unit 3. The sample rack L accommodating the sample container, in which the aspiration of the sample is completed, is transferred to the post-analysis rack sending position 461 by the rack transporting portion 43, and sent to the post-analysis rack holding portion 42 by the rack sending portion 46. When a plurality of sample racks L is mounted on the pre-analysis rack holding portion 41, the sample rack L accommodating the sample completed with the analysis is sequentially sent to the post-analysis rack holding portion 42 by the rack sending portion 46, and the plurality of sample racks L are accumulated in the post-analysis rack holding portion 42.

<Configuration of Information Processing Unit>

Figure 5:
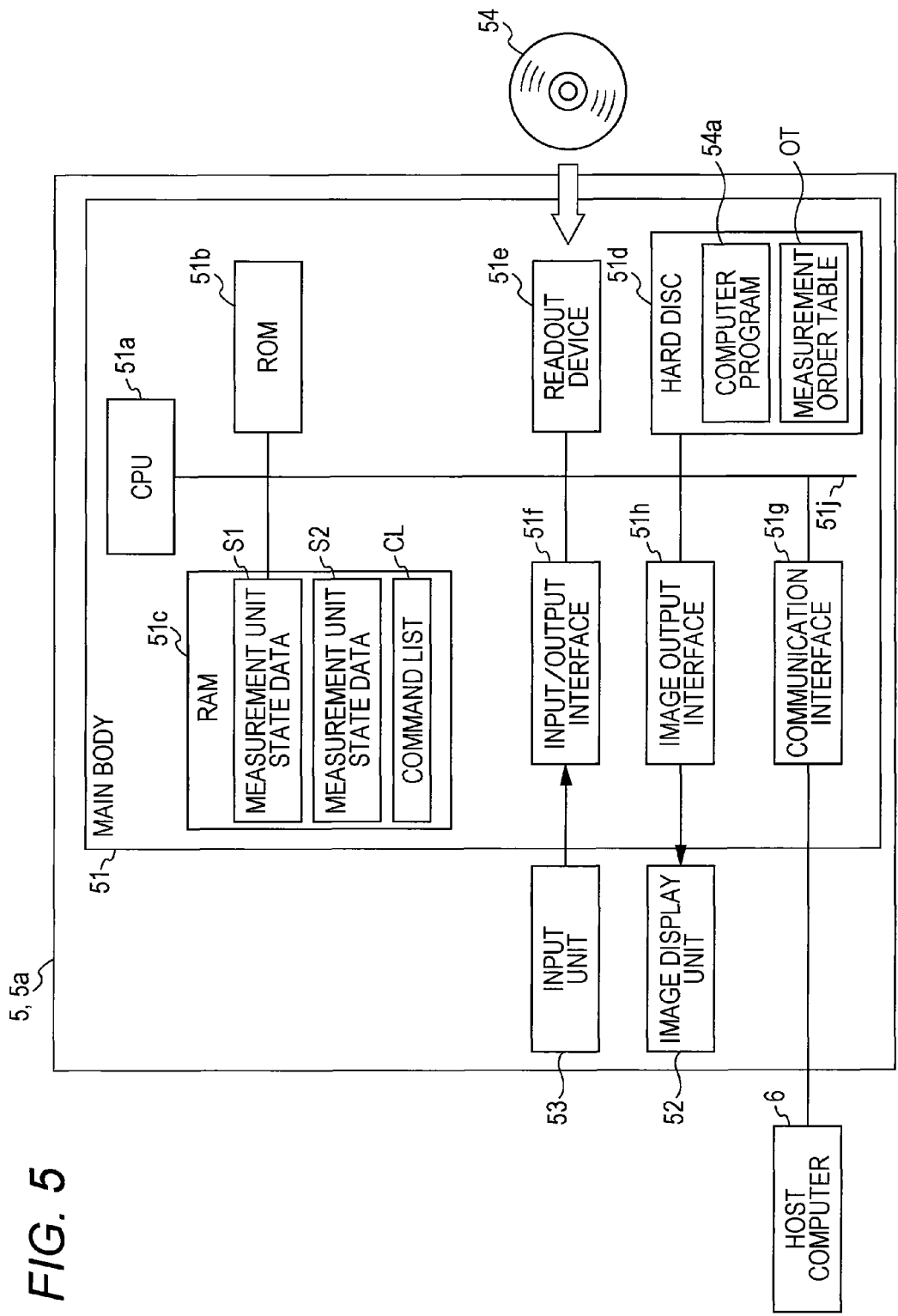
FIG. 5 is a block diagram showing the configuration of an information processing unit arranged in the sample analyzer according to the embodiment.

The configuration of the information processing unit 5 will now be described. The information processing unit 5 is configured by a computer. FIG. 5 is a block diagram showing a configuration of the information processing unit 5. The information processing unit 5 is configured by a computer 5*a*. As shown in FIG. 5, the computer 5*a* includes a main body 51, an image display unit 52, and an input unit 53. The main body 51 includes a CPU 51*a*, a ROM 51*b*, a RAM 51*c*, a hard disc 51*d*, a read-out device 51*e*, an input/output interface 51*f*, a communication interface 51*g*, and an image output interface 51*h*, where the CPU 51*a*, the ROM 51*b*, the RAM 51*c*, the hard disc 51*d*, the read-out device 51*e*, the input/output interface 51*f*, the communication interface 51*g*, and the image output interface 51*h* are connected by a bus 51*j*.

The read-out device 51*e* can read out the computer program 54*a* for functioning the computer as the information processing unit 5 from the portable recording medium 54, and install the computer program 54*a* in the hard disc 51*d*.

The RAM 51*c* includes measurement unit state data regions S1 and S2 respectively which indicate the states of the first measurement unit 2 and the second measurement unit 3. The data of one of "sample container retrievable", "sample container not retrievable/returnable", and "sample container returnable" is held in the measurement unit state data regions S1, S2. If the measurement unit is in the standby state in which the retrieval of the sample container T and the measurement of the sample are not performed and is waiting for the retrieval of the sample container, the state of such measurement unit is "sample container retrievable". If the measurement unit is performing the retrieval of the sample container, the state of such measurement unit is "sample container not retrievable/returnable". If the measurement unit is in a state the aspiration of the sample from the retrieved sample container T is finished and is waiting for the sample container T to be returned to the sample rack L, the state of such measurement unit is "sample container returnable". When the measurement unit is measuring the measurement specimen by the detecting portions 23, 33 (that is, detecting the blood cells) and the return of the sample container T is completed, the state of such measurement unit is the "sample container retrievable" at which a new sample container can be retrieved. The operation state data indicating such operation state is acquired in real time by the CPU 51*a*, and the most recent operation state data is stored in the measurement unit state data regions S1, S2.

The RAM 51*c* includes a region of command list CL for storing the commands related to the transportation of the sample. The information processing unit 5 of the sample analyzer 1 according to the present embodiment can execute "rack sending command", "rack ID reading command", "sample information assigning command", "sample container retrieving command", "sample container returning command", and "rack discharging command", as the command related to the transportation of the sample. The "rack sending command", the "rack ID reading command", and the "rack discharging command" are commands targeted on the sample rack, and the "rack sending command", the "rack ID reading command", and the "rack discharging command" are respectively generated with respect to one sample rack. The "sample information assigning command", the "sample container retrieving command", and the "sample container returning command" are commands targeting on the sample container, and the "sample information assigning command", the "sample container retrieving command", and the "sample container returning command" are respectively generated with respect to one sample container.

The "rack sending command" is the command for instructing the operation to send the sample rack L held in the pre-analysis rack holding portion 41 to the rack transport path 43. The "rack ID reading command" is the command for instructing the operation to transport the sample rack L sent to the rack transport path 43 to the position where the barcode reading portion 44 can read the rack barcode along the rack transport path 43, and read the rack ID with the barcode reading portion 44. The "sample information assigning command" is the command for instructing the operation to transport the sample rack along the rack transport path 43 until the target sample container (holding position) is positioned at the barcode reading position 43*d*, determine the presence of the sample container with the sample container sensor 45, read the sample ID by the barcode reading portion 44, and acquire the measurement order from the read sample ID. The "sample container retrieving command" is the command for instructing the operation to transport the sample rack L along the rack transport path 43 until the target sample container (holding position) is positioned at the first sample supply position 43*a* or the second sample supply position 43*b*, and have the first measurement unit 2 or the second measurement unit 3 retrieve the sample container T. The "sample container returning command" is the command for instructing the operation to transport the sample rack L along the rack transport path 43 until the holding position where the target sample container is held is positioned at the first sample supply position 43*a* or the second sample supply position 43*b*, and return the sample container retrieved to the first measurement unit 2 or the second measurement unit 3 to the holding position. The "rack discharging command" is the command for instructing the operation to transport the sample rack L to the rack sending position 461 along the rack transport path 43, and send the sample rack L from the rack sending position 461 to the post-analysis rack holding portion 42.

A predetermined priority is assigned to each of such commands. In the measurement of the sample, the CPU 51*a* of the information processing unit 5 registers the commands to be executed in the command list CL, sorts the commands in order of priority in the command list CL, and executes the command within the highest priority of the executable commands registered in the command list CL. The execution of the command will be described later.

The hard disc 51*d* include a measurement order table OT storing the measurement orders of the samples. The information processing unit 51 transmits request data of the measurement order with the sample ID and the like as the key to the host computer communicably connected through the communication interface 51*f*, and receives the measurement order transmitted from the host computer in response. The measurement order received in such manner is stored in the measurement order table OT.

[Operation of Sample Analyzer 1]

The operation of the sample analyzer 1 according to the present embodiment will be described below.

<Sample Transport Controlling Process>

Figure 6:
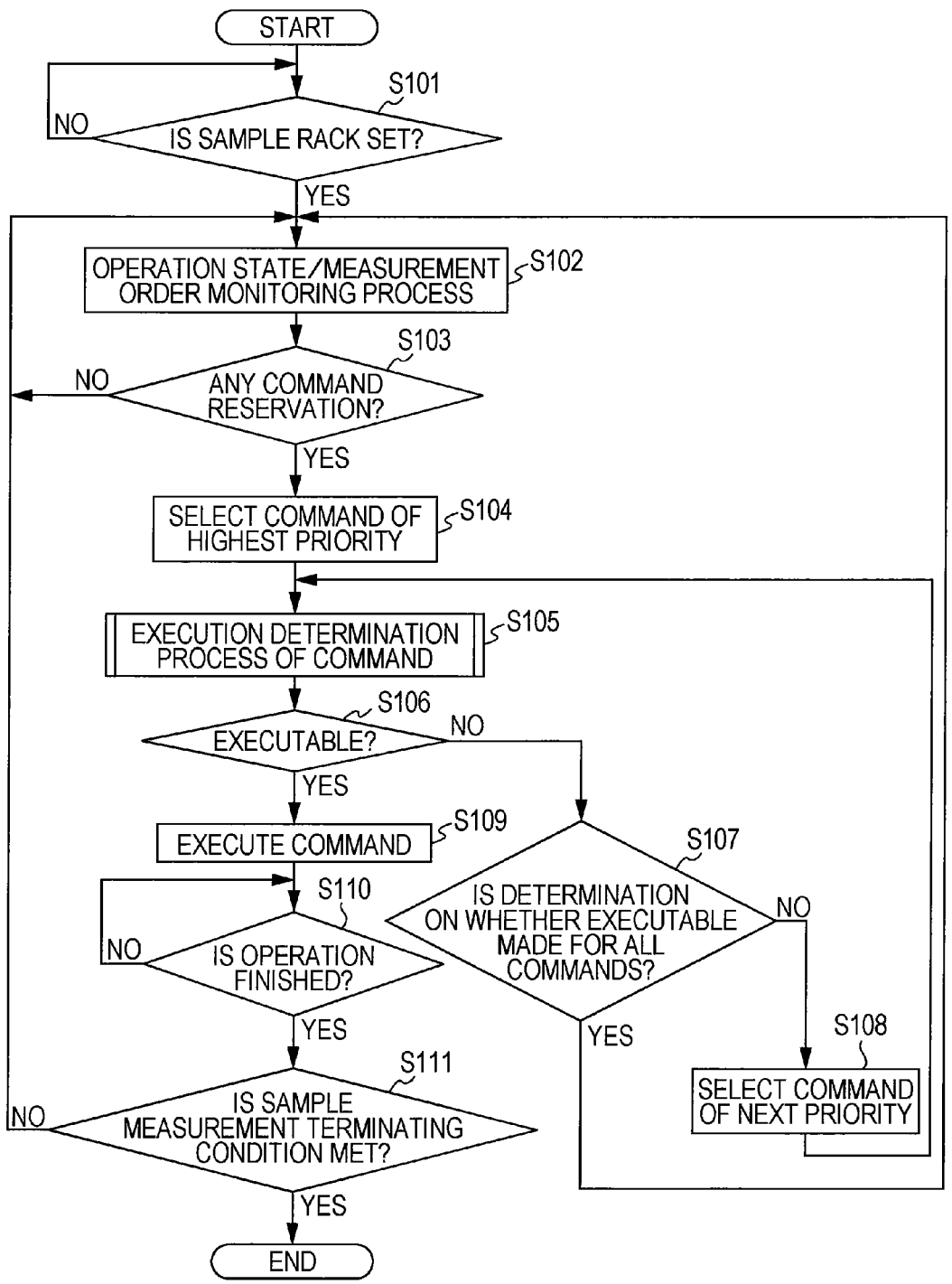
FIG. 6 is a flowchart showing the flow of the sample transport controlling process by the information processing unit of the sample analyzer according to the embodiment.

FIG. 6 is a flowchart showing the flow of the sample transport controlling process by the information processing unit 5 of the sample analyzer 1. The operator places the sample rack L holding a plurality of sample containers T accommodating the sample in the pre-analysis rack holding portion 41. The operator operates the input unit 53 in this state to instruct the execution of the sample measurement to the information processing unit 5. The CPU 51*a* of the information processing unit 5 thereby executes the sample transport controlling process and the command reservation process described below.

The CPU 51*a* of the information processing unit 5 executes the following sample transport controlling process after accepting the instruction to execute the sample measurement. First, the CPU 51*a* determines whether or not the sample rack L placed in the pre-analysis rack holding portion 41 is detected by a sensor (not shown) (step S101). If detection is not made that the sample rack L is set in the pre-analysis rack holding portion 41 (NO in step S101), the CPU 51*a* repeats the process of step S101. If detection is made that the sample rack L is set in the pre-analysis rack holding portion 41 (YES in step S101), the CPU 51*a* executes the operation state/measurement order monitoring process (step S102). In the operation state/measurement order monitoring process, the CPU 51*a* references the measurement unit state data regions S1, S2 to acquire the operation state data indicating the operation states of the first measurement unit 2 and the second measurement unit 3 at the relevant time point, and also references the measurement order table OT to acquire the measurement order registered at the relevant time point.

The CPU 51*a* then determines whether or not a command is reserved, that is, whether or not a command is registered in the command list CL in the command reservation process to be described later (step S103). If the command is not reserved (NO in step S103), the CPU 51*a* returns the process to step S102. If the command is reserved (YES in step S103), the CPU 51*a* selects the command with the highest priority out of the commands registered in the command list CL (step S104), and executes the execution determination process of the command (step S105).

Figure 7:
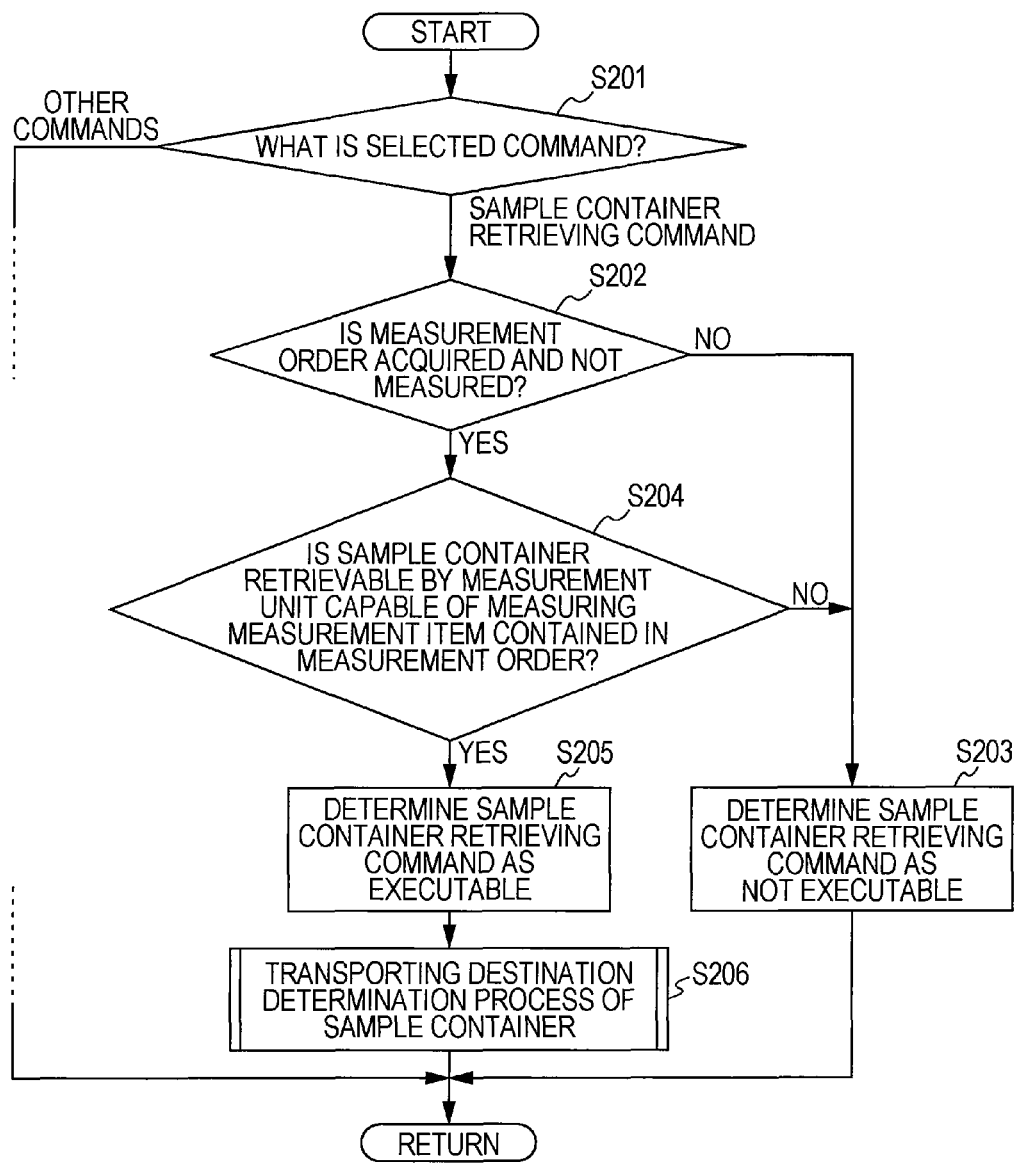
FIG. 7 is a flowchart showing the flow of the execution determination process of the command by the information processing unit of the sample analyzer according to the embodiment.

FIG. 7 is a flowchart showing the flow of the execution determination process of the command. In the execution determination process of the command, the CPU 51*a* first determines what command is selected (step S201). Whether or not the command can be executed is determined according to the selected command. To simplify the description, the determination on whether or not the sample container retrieving command can be executed will be described below, and other commands will be omitted. If the selected command is the sample container retrieving command in step S201 ("sample container retrieving command" in step S201), the CPU 51*a* determines whether the measurement order is acquired and whether the relevant sample is non-measured for the sample container T (sample) or the target of the relevant command (step S202). In the process, whether or not the measurement order is already acquired is determined by the measurement order monitored in step S102. If the measurement order is not acquired or the sample is already measured in step S202 (NO in step S202), the CPU 51*a* determines that the relevant command cannot be executed (step S203), and returns the process to the call out address of the execution determination process of the command in the main routine.

If the measurement order is acquired and the sample is not measured in step S202 (YES in step S202), the CPU 51*a* determines whether or not the measurement unit that can measure the measurement item contained in the measurement order is in the state of "sample container retrievable" (step S204). In this process, the CPU 51*a* checks the measurement item contained in the measurement order, and specifies the measurement unit that can measure the measurement item out of the first measurement unit 2 and the second measurement unit 3. For instance, the first measurement unit 2 and the second measurement unit 3 are both specified as the measurement unit capable of measuring the relevant measurement item if the measurement item is the CBC+DIFF item, and the second measurement unit 3 is specified as the measurement unit capable of measuring the relevant measurement item if the measurement item is the CBC+DIFF item and the RET. The CPU 51*a* also determines whether or not the state of the measurement unit specified in such manner is "sample container retrievable". The operation state data acquired in step S102 is used therefor, where whether or not the operation state data of the first measurement unit 2 and the second measurement unit 3 read out from the measurement unit state data regions S1, S2 are respectively "sample container retrievable" is determined if the specified measurement unit is the first measurement unit 2 and the second measurement unit 3, and whether or not the operation state data of the second measurement unit 3 read out from the measurement unit state data region S2 is "sample container retrievable" is determined if the specified measurement unit is the second measurement unit 3.

If the operation state of the measurement unit capable of measuring the measurement item contained in the measurement order is "sample container not retrievable/returnable" and "sample container returnable" in step S204 (NO in step S204), the CPU 51*a* determines that the command is not executable (step S203), and returns the process to the call out address of the execution determination process of the command in the main routine.

If the operation state of the measurement unit capable of measuring the measurement item contained in the measurement order is "sample retrievable" in step S204 (YES in step S204), the CPU 51*a* determines that the "sample container retrieving command" being selected is executable (step S205), and executes the transporting destination determination process of the sample container (step S206). After the transporting destination determination process of the sample container is finished, the CPU 51*a* returns the process to the call out address of the execution determination process of the command in the main routine.

Figure 8:
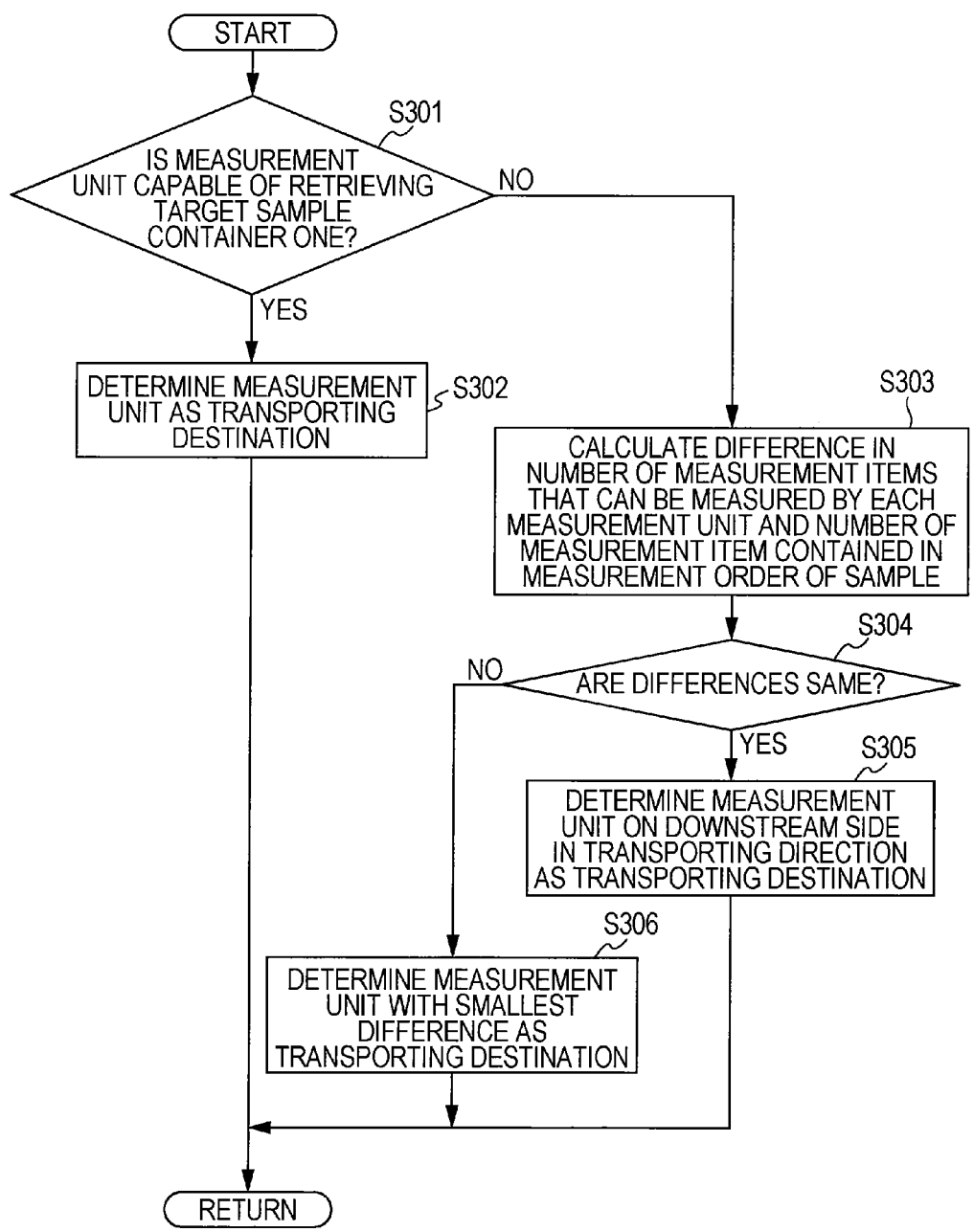
FIG. 8 is a flowchart showing the flow of the transporting destination determination process of the sample container by the information processing unit of the sample analyzer according to the embodiment.

FIG. 8 is a flowchart showing the flow of the transporting destination determination process of the sample container. In the transporting destination determination process of the sample container, the CPU 51*a* first determines whether the number of measurement units that can retrieve the sample container, or the target of the command, is one (step S301). In the process, the number of measurement units that can measure all the measurement items contained in the measurement order of the sample and its operation state is "sample container retrievable" is specified, and whether or not such number is one is determined. For instance, when the measurement item is CBC+DIFF item, the measurement unit that can measure the relevant measurement item is the first measurement unit 2 and the second measurement unit 3, and thus the number is "2" if the operation state data of the first measurement unit 2 and the second measurement unit 3 are both "sample container retrievable", and the number is "1" if only one of the operation state data is "sample container retrievable". When the measurement item is CBC+DIFF item and RET, the measurement unit that can measure the relevant measurement item is the second measurement unit 3, and thus the number is "1" if the operation state data of the second measurement unit 3 is "sample container retrievable".

If the number of measurement units that can retrieve the sample container or the target of the selected command is one in step S301 (YES in step S301), the CPU 51a determines the relevant measurement unit as the transporting destination (step S302), and returns the process to the call out address of the transporting destination determination process of the sample container in the execution determination process of the command.

If the number of measurement units that can retrieve the sample container or the target of the selected command is not one in step S301 (NO in step S301), the CPU 51a calculates the difference of the number of measurement items that can be measured by each measurement unit and the number of measurement items contained in the measurement order of the sample (step S303). For instance, when the measurement item contained in the measurement order is CBC+DIFF item, the number of measurement items of the first measurement unit 2 is "2" and the number of measurement items contained in the measurement order is "2", and hence the difference (difference for the first measurement unit 2) becomes "0". The difference (difference for the second measurement unit 3) is "2" since the number of measurement items of the second measurement unit 3 is "4". Description will be made below assuming the CBC item and the DIFF item are one item each.

The CPU 51a determines whether or not the difference for the first measurement unit 2 and the difference for the second measurement unit 3 obtained in the above manner are the same (step S304). If the differences are the same (YES in step S304), the CPU 51a determines the second measurement unit 3 or the measurement unit on the downstream side in the transporting direction (post-analysis rack holding portion 42 side) of the rack transport path 43 as the transporting destination (step S305), and returns the process to the call out address of the transporting destination determination process of the sample container. A space on the rack transport path 43 on the pre-analysis holding portion 41 side thus can be opened, whereby the sample rack L transported to the second measurement unit 3 side can be transported to the rack transport path 43 at a timing faster than the following sample rack L as long as a it does not need to be subsequently transported to the first measurement unit 2 side. If the differences are not the same (NO in step S304), the CPU 51a determines the measurement unit with the smallest difference as the transporting destination (step S306), and returns the process to the call out address of the transporting destination determination process of the sample container. For instance, if the difference for the first measurement unit 2 is "0" and the difference for the second measurement unit 3 is "2", the first measurement unit 2 having the smallest difference is determined as the transporting destination. The measurement unit with greater number of measurement items that can be measured is thus in an open state, so that the measurement wait time of the sample can be reduced when the sample that can be measured only with the relevant measurement unit appeared.

Returning back to FIG. 6, the CPU 51a determines whether or not the selected command is determined as executable in the execution determination process of the command (step S106), where whether or not the determination on executable or not is made for all reserved commands (i.e., all commands registered in the command list CL) is finished is determined (step S107) if determined that the command is not executable (NO in step S106). If the command in which the determination on executable or not is not made exists (NO in step S107), the CPU 51a selects the command having the next highest priority to the command being selected at the relevant time point (step S108) and proceeds the process to step S105. If the determination on executable or not is finished for all reserved commands (YES in step S107), the CPU 51a proceeds the process to step S102.

If the selected command is executable in step S106 (YES in step S106), the CPU 51a executes the relevant command (step S109). In this process, the CPU 51a deletes the relevant command from the command list CL with the execution of the command. The CPU 51a then determines whether or not the operation instructed by the command is completed (step S110). For instance, when the "sample container retrieving command" is selected, the sample rack L is transported along the rack transport path 43 until the target sample container (holding position) is positioned at the first sample supply position 43a or the second sample supply position 43b, and whether or not the first measurement unit 2 or the second measurement unit 3 has completed the operation of retrieving the sample container T is determined. If the operation is not completed (NO in step S110), the process of step S110 is repeated until the operation is completed.

If the operation is completed in step S110 (YES in step S110), the CPU 51a determines whether or not the sample measurement terminating condition is met (step S111). The sample measurement terminating condition is that the sample rack is not present in the pre-analysis rack holding portion 41 and the sample rack is not present on the rack transport path 43. If the sample measurement terminating condition is not met (NO in step S111), the CPU 51a returns the process to step S102. If the sample measurement terminating condition is met (YES in step S111), the CPU 51a terminates the process.

<Command Reservation Process>

Figures 9, 10:
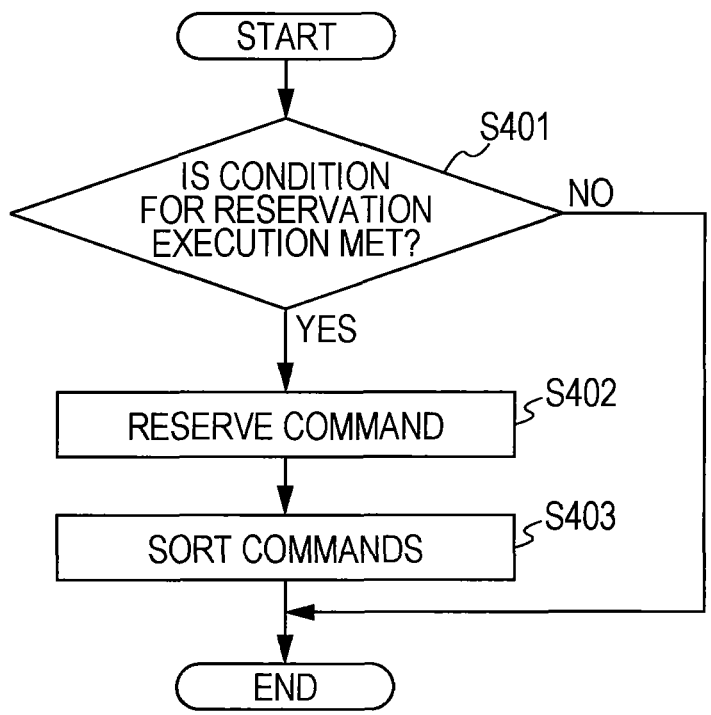
FIG. 9 is a flowchart showing the flow of the command reservation process by the information processing unit of the sample analyzer according to the embodiment.
FIG. 10 is a schematic view for describing the priority of the commands.

The command reservation process of the command by the information processing unit 5 will now be described. FIG. 9 is a flowchart showing the flow of the command reservation process by the information processing unit 5 of the sample analyzer 1. The CPU 51a first determines whether or not the condition for reservation execution is met (step S401), and reserves the command, that is, registers the command to the command list CL (step S402) if the condition for reservation execution is met (YES in step S401).

The reservation execution condition will be described below. The reservation execution condition of the command differs for every command. The reservation execution condition of the "rack sending command" differs for when the rack sending command is reserved the first time after the instruction to execute the sample measurement is provided, and for when the rack sending command is reserved after the second time. The reservation execution condition of the first rack sending command includes receiving the instruction to execute the sample measurement. Therefore, when the instruction to execute the sample measurement is accepted, the first rack sending command is immediately reserved. The reservation execution condition of the second and subsequent rack sending command includes sending the preceding sample rack from the pre-analysis rack holding portion 41 to the rack transport path 43. The reservation execution condition of the "rack ID reading command", the "sample information assigning command", and the "rack discharging command" includes sending the sample rack from the pre-analysis rack holding portion 41 to the rack transport path 43, same as the second and subsequent "rack sending command". Therefore, when the preceding sample rack is sent from the pre-analysis rack holding portion 41 to the rack transport path 43, the "rack ID reading command" for the relevant sample rack, the "sample information assigning command" for all holding positions of the relevant sample rack, the "rack discharging command" for the relevant sample rack, and the "rack sending command" for the next sample rack are reserved. The reservation execution condition of the "sample container retrieving command" includes confirmation of the sample ID and the measurement order for the target sample container (holding position). The reservation execution condition of the "sample container returning command" includes retrieving of the target sample container to the measurement unit.

As described above, the "rack sending command", the "rack ID reading command", and the "rack discharging command" are commands targeting on the sample rack, where the "rack sending command", the "rack ID reading command", and the "rack discharging command" are respectively reserved one each for one sample rack. For instance, when the reservation execution condition of the "rack sending command" is met, one "rack sending command" is registered to the command list CL. The "sample information assigning command", the "sample container retrieving command", and the "sample container returning command" are commands targeting on the sample container (holding position), and the "sample information assigning command", the "sample container retrieving command", and the "sample container returning command are respectively reserved one each for one sample container. For instance, when the reservation execution condition of "the sample rack is sent from the pre-analysis rack holding portion 41 to the rack transport path 43" of the "sample information assigning command" is met, ten "sample information assigning commands" corresponding to all holding positions of the sample racks L are registered in the command list CL. Each "sample information assigning command" includes information indicating the holding position as the attribute information. For instance, the "sample information assigning command" corresponding to the holding position 1 contains information indicating the holding position "1" as the attribute information. Similarly, the "sample container retrieving command" and the "sample container returning command" also include the information indicating the corresponding holding position as the attribute information.

As described above, the "sample information assigning command", the "sample container retrieving command", and the "sample container returning command" include the attribute information indicating the target sample container (holding position), and hence if one of the "sample information assigning command", the "sample container retrieving command", and the "sample container returning command" is selected in the sample transport control process, the sample container (holding position) corresponding to the command is selected at the same time as when the operation instruction is selected.

After the command is reserved as described above, the CPU 51a sorts the commands in the command list CL (step S403). In this process, each command is sorted in the order of priority. FIG. 10 is a schematic view for describing the priority of the commands. As shown in FIG. 10, the "rack discharging command" has the first priority, the "rack sending command" has the second priority, the "rack ID reading command" has the third priority, the "sample container retrieving command" has the fourth priority, the "sample container returning command" has the fifth priority and the "sample information assigning command" has the sixth priority.

Furthermore, if a plurality of "sample container retrieving commands" is registered in the command list CL, a command in which the number of measurement units that can measure the sample (i.e., that can measure all the measurement items contained in the measurement order of the sample) accommodated in the target sample container is small is prioritized among the "sample container retrieving command". For instance, when the "sample container retrieving commands" of the holding positions 1 and 2 are registered in the command list CL, and the measurement order of the sample at the holding position 1 includes the CBC+DIFF item and the measurement order of the sample at the holding position 2 includes the CBC+DIFF item and the RET, the first measurement unit 2 and the second measurement unit 3 can respectively measure the sample at the holding position 1 and only the second measurement unit 3 can measure the sample at the holding position 2, and hence the "sample container retrieving command" targeting the sample container at the holding position 2 is prioritized. If the priority among the "sample container retrieving commands" still cannot be determined, the "sample container retrieving command" targeting the sample container with the small number of the holding position, that is, the sample container positioned on the downstream side in the transporting direction (post-analysis rack holding portion 42 side) in the rack transport path 43 is prioritized. For instance, when the "sample container retrieving commands" of the holding positions 1 and 3 are registered in the command list CL, and the measurement order of the samples at the holding positions 1 and 3 respectively include the CBC+DIFF item, the samples at the holding positions 1 and 3 can be measured by both the first measurement unit 2 and the second measurement unit 3 and thus the priority cannot be determined. In this case, the "sample container retrieving command" targeting on the sample container of the holding position 1 with small holding position number is prioritized.

After the commands in the command list CL are sorted according to such rules, the CPU 51a terminates the command reservation process. The CPU 51a also terminates the command reservation process when the condition for the reservation execution is not met in step S401 (NO in step S401).

<Operation Example>

The transporting operation of the sample container of the sample analyzer 1 will be specifically described below using an example. In the following description, the operation of the sample analyzer 1 when the sample rack L holding the samples for which the measurement order includes the CBC+DIFF item at the holding positions 1 to 5, and the samples for which the measurement order includes the CBC+DIFF item, the RET, and the NRBC at the holding positions 6 to 10 is inserted to the sample analyzer 1 will be described. To simplify the description, the description on the "rack discharging command", the "rack ID reading command", and the "sample container returning command" will be omitted.

Figure 11A:
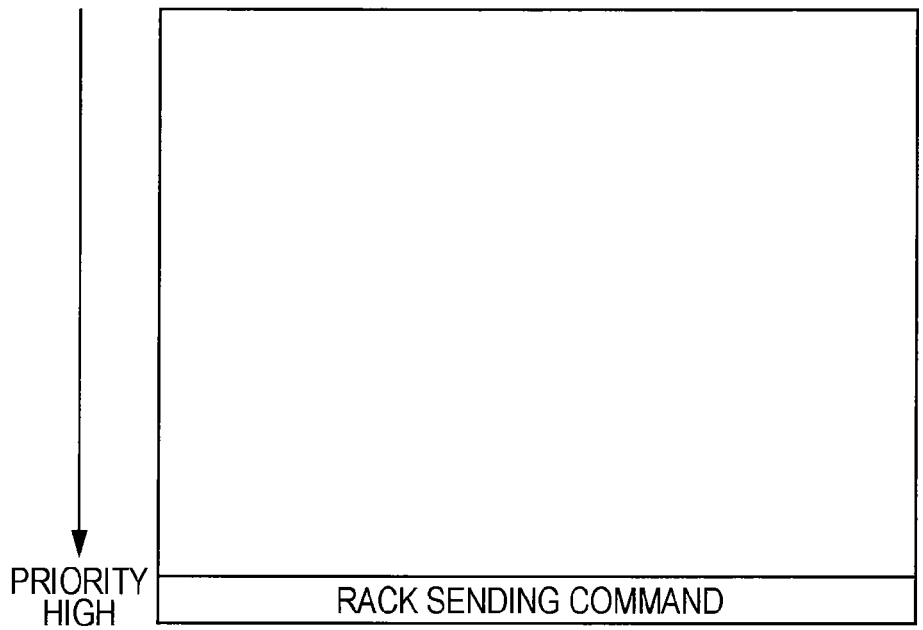
FIGS. 11A to 11G are schematic views showing the state of the command list.

First, the instruction to execute the sample measurement is input to the information processing unit 5 by the user. The reservation execution condition of the "rack sending command" is thus met (YES in step S401 of FIG. 9), and hence the "rack sending command" is registered in the command list CL (step S402), as shown in FIG. 11A. Although the commands are sorted at this point, the order does not change since only one command is registered in the command list CL (step S403).

The "rack sending command" is then executed (step S109). The sample rack L is thereby sent to the rack transport path 43 by the rack sending portion 41b. When the "rack sending command" is executed, the "rack sending command" is deleted from the command list CL.

Figure 11B:
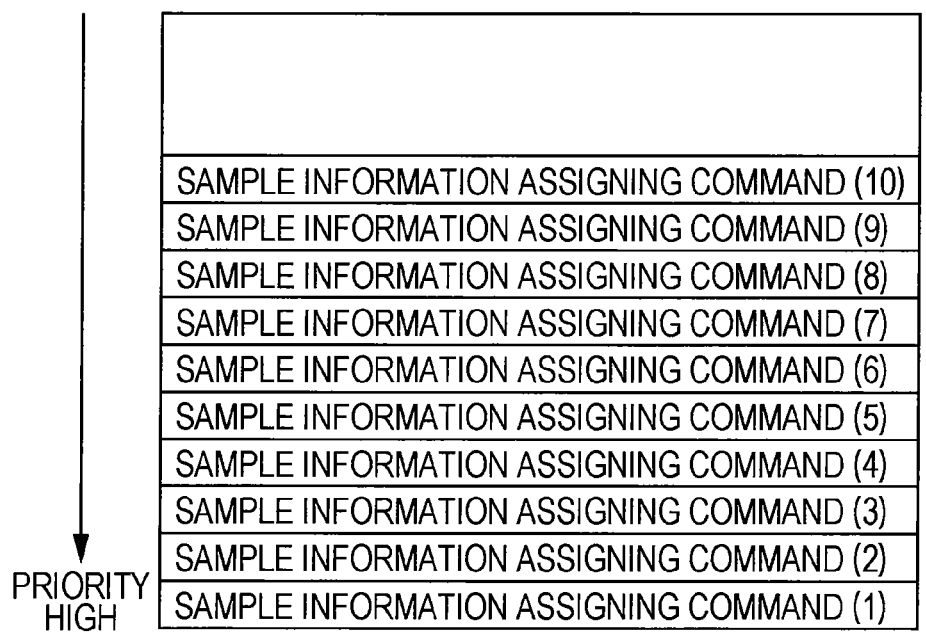

After the rack sending operation is completed (YES in step S110), the "sample information assigning command" for ten containers are registered to the command list CL, as shown in FIG. 11B. The "sample information assigning command" is the command targeting on the holding position (sample container), and thus a total of ten "sample information assigning commands" are registered to the command list CL, one for each holding position 1 to 10. In FIG. 11B, the number in ( ) represents the holding position number serving as the target of the command. The priority is higher the smaller the holding position number among the ten "sample information assigning commands". Thus, the commands in the command list CL are sorted in the order of small holding position number.

The "sample information assigning command (1)" targeting on the holding position 1 with the highest priority is then executed (step S109). Specifically, the sample rack is transported along the rack transport path 43 until the sample container of the holding position 1 is positioned at the barcode reading position 43d, and the presence of the sample container is first determined by the sample container sensor 45. After the sample container T is detected, the sample ID is read by the barcode reading portion 44. The measurement order is then requested to the host computer 6 by the read sample ID, and the measurement order is acquired. As described above, the measurement order of the sample of the holding position 1 includes the CBC+DIFF item. The acquired measurement order is stored in the measurement order table OT. When the "sample information assigning command (1)" is executed, the "sample information assigning command (1)" is deleted from the command list CL.

Figure 11C:
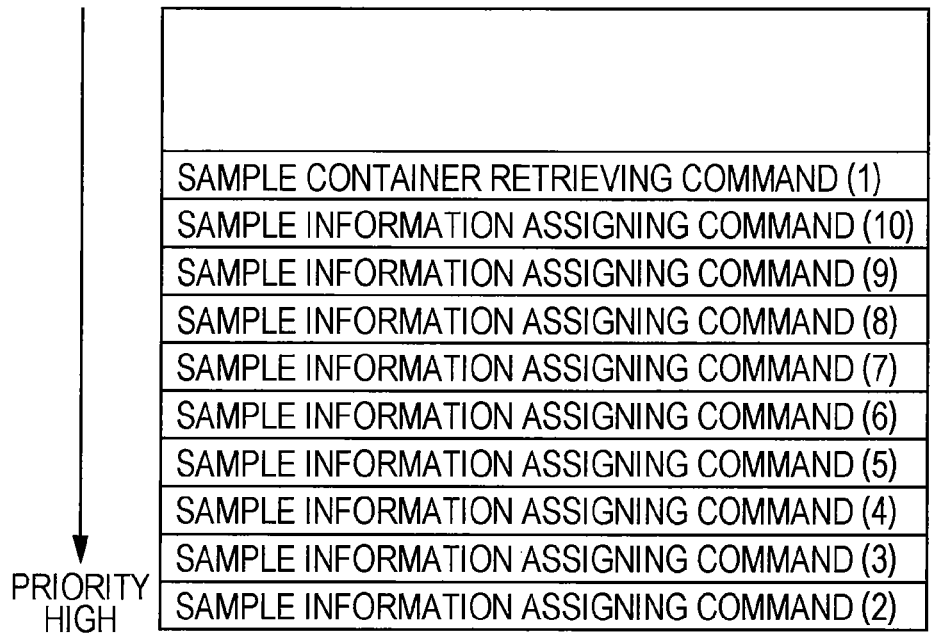

After the sample information assigning operation is completed (YES in step S110), the "sample container retrieving command (1)" is additionally registered to the command list CL. The state of the command list CL in this case is shown in FIG. 11C.

Figure 11D:
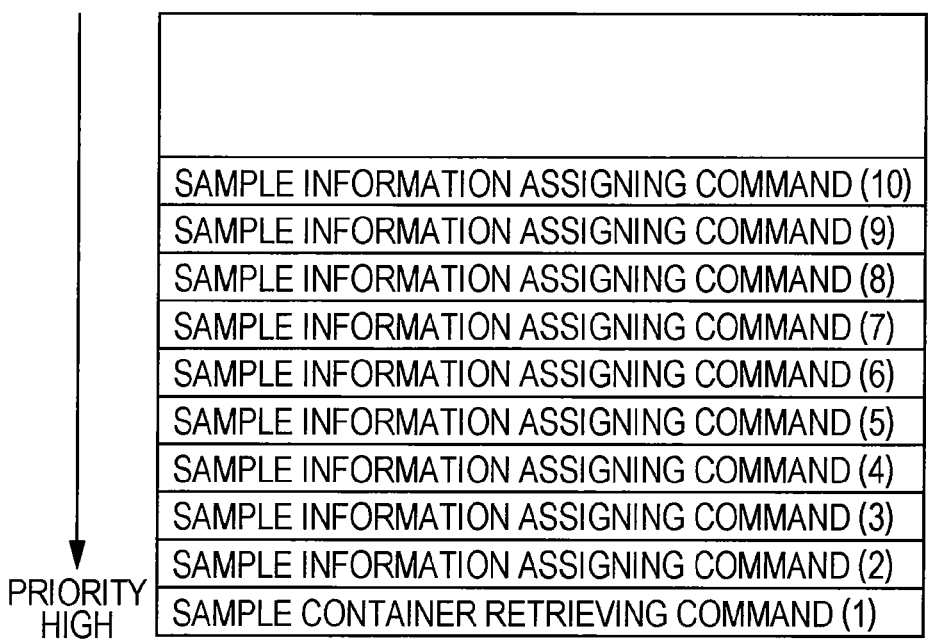

The commands are then sorted. FIG. 11D is a schematic view showing the state of the command list CL after the sorting of the commands is carried out from the state shown in FIG. 11C. Since the priority of the "sample container retrieving command" is higher than the priority of the "sample information assigning command", the "sample container retrieving command (1)" is moved to the front side (lower side in the figure) than the "sample information assigning command".

The "sample container retrieving command (1)" targeting on the sample container of the holding position 1 having the highest priority is then selected (step S108).

The measurement order of the sample of the holding position 1 includes the CBC+DIFF item, and the measurement unit that can measure such items is the first measurement unit 2 and the second measurement unit 3. At this time point, the first measurement unit 2 and the second measurement unit 3 are both in the "sample container retrievable" state (YES in step S204). Therefore, determination is made that the "sample container retrieving command (1)" is executable (step S205), and the transporting destination determination process of the sample container is executed (step S206).

In the transporting destination determination process of the sample container, the number of measurement units that can retrieve the target sample container is "2" (NO in step S301). Therefore, the difference between each number of measurement items that can be measured by the first measurement unit 2 and the second measurement unit 3 and the number of measurement items contained in the measurement order is calculated (step S303). Here, the number of measurement items (CBC+DIFF item) of the first measurement unit 2 is "2" and the number of measurement items (CBC+DIFF item) contained in the measurement order is "2", and thus the difference is "0". The number of measurement items of the second measurement unit 3 is "4", on the other hand, and thus the difference is "2". Therefore, the difference is not the same (NO in step S304), and hence the first measurement unit 2 or the measurement unit with the smallest difference is determined as the transporting destination (step S306).

The "sample container retrieving command (1)" is executed (step S109), the sample rack L is transported along the rack transport path 43 until the sample container of the holding position 1 is positioned at the first sample supply position 43a, and the sample container T is retrieved from the sample rack L by the first measurement unit 2. Thereafter, the sample in the sample container T is stirred, the sample is aspirated from the sample container T, and the measurement of the sample is carried out. When the "sample container retrieving command (1)" is executed, the "sample container retrieving command (1)" is deleted from the command list CL.

After the sample container retrieving operation is completed (YES in step S110), the "sample information assigning command (2)" targeting on the holding position 2 registered in the command list CL is executed (step S109). The measurement order of the sample accommodated in the sample container of the holding position 2 is thereby acquired. As described above, the measurement order of the sample of the holding position 2 includes the CBC+DIFF item. The acquired measurement order is stored in the measurement order table OT. When the "sample information assigning command (2)" is executed, the "sample information assigning command (2)" is deleted from the command list CL.

Figure 11E:
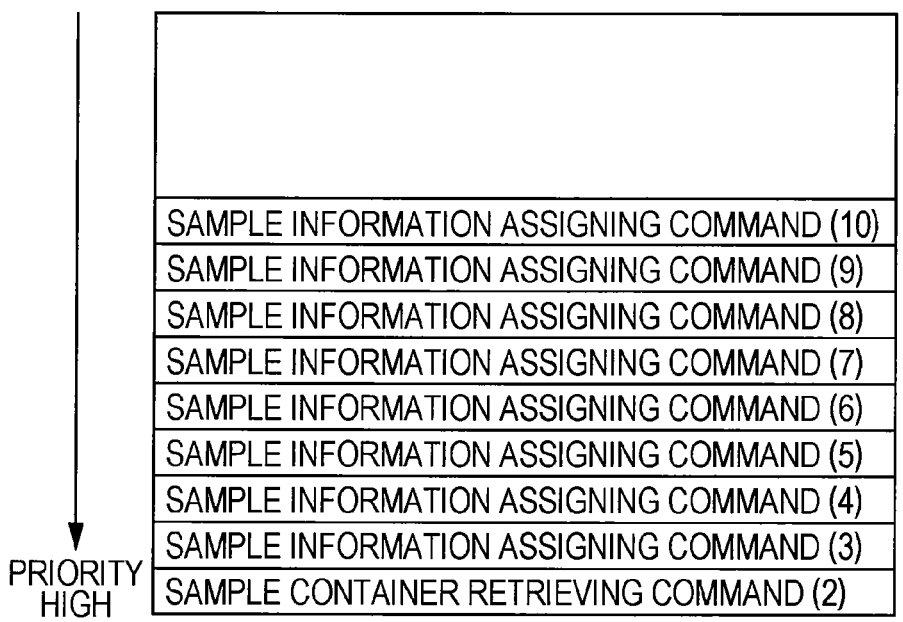

After the sample information assigning operation is completed (YES in step S110), the "sample container retrieving command (2)" is additionally registered to the command list CL, and the commands are sorted. FIG. 11E shows the command list CL after the sorting. Since the priority of the "sample container retrieving command" is higher than the priority of the "sample information assigning command", the "sample container retrieving command (2)" is moved to the front side (lower side in the figure) than the "sample information assigning command".

The execution determination process of the "sample container retrieving command (2)" targeting on the sample container of the holding position 2 having the highest priority is then carried out, where the "sample container retrieving command (2)" is executed when determined as executable. When the "sample container retrieving command (2)" is executed, the "sample container retrieving command (2)" is deleted from the command list CL. At this time point, the first measurement unit 2 is in the "sample container not retrievable/returnable" state, and the second measurement unit 3 is in the "sample container retrievable" state, and thus the sample container of the holding position 2 is transported to the second measurement unit 3.

After the sample container retrieving operation by the second measurement unit 3 is completed (YES in step S110), the first measurement unit 2 and the second measurement unit 3 are both in the "sample container not retrievable/returnable" state at this time point. The measurement orders of the samples of the holding positions 1 and 2 are stored in the measurement order table OT.

Thereafter, the "sample information assigning command" registered in the command list CL is sequentially executed from the small holding position number as long as the operation states of the first measurement unit 2 and the second measurement unit 3 maintain the state of "sample container not retrievable/returnable". In the present example, the operation states of the first measurement unit 2 and the second measurement unit 3 are assumed to be in the state of "sample container not retrievable/returnable" until the execution of the "sample information assigning command" targeting on the holding positions 3 to 10 is completed.

Figure 11F:
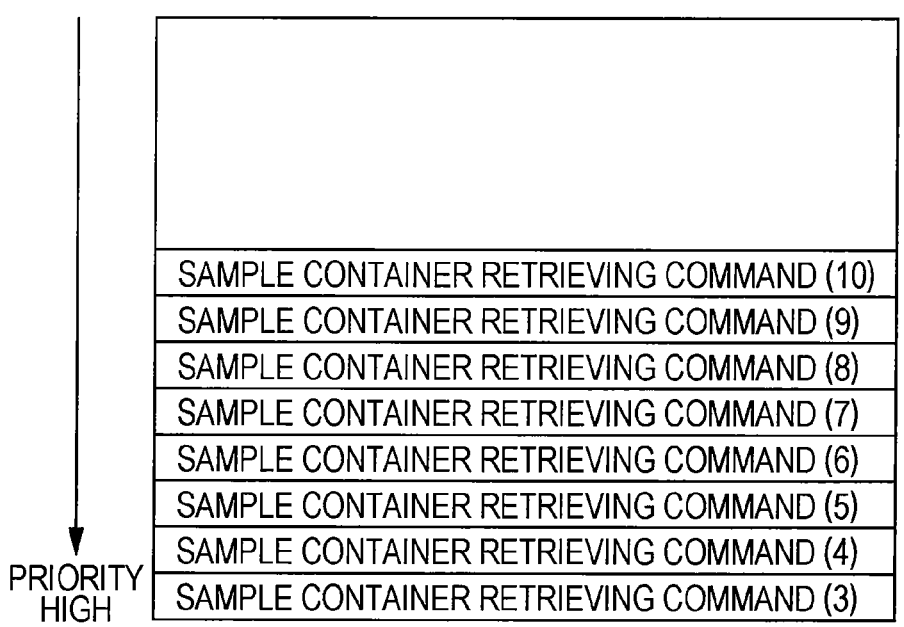

FIG. 11F is a schematic view showing a state of the command list CL immediately after the execution of the "sample information assigning command" targeting on the sample containers of the holding positions 3 to 10.

Figure 11G:
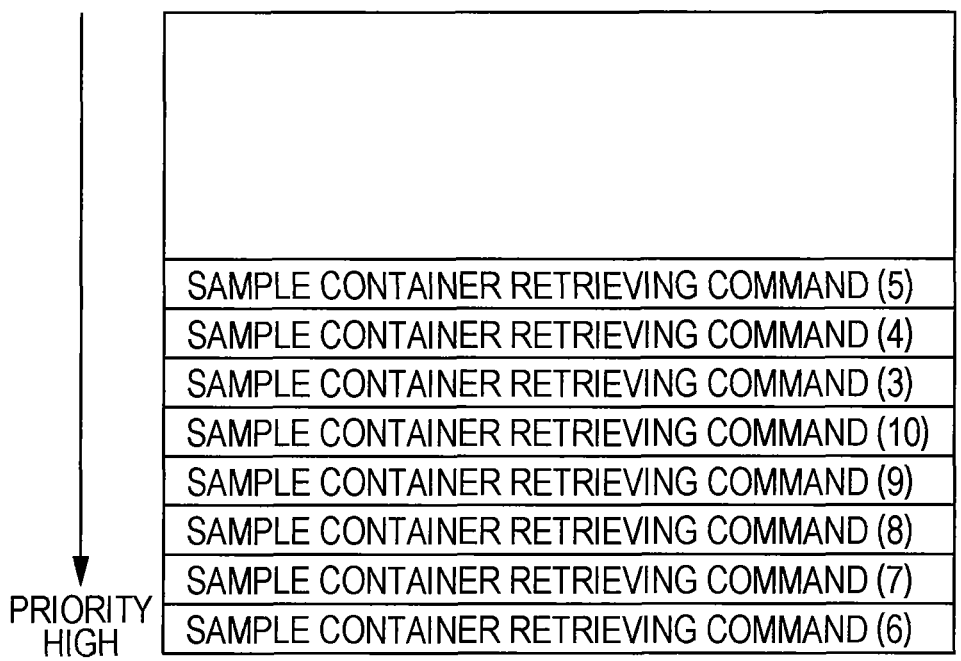

The commands are then sorted. Furthermore, if a plurality of "sample container retrieving commands" is registered in the command list CL, a command in which the number of measurement units that can measure the sample (i.e., that can measure all the measurement items contained in the measurement order of the sample) accommodated in the target sample container is small is prioritized among the "sample container retrieving command". If the priority among the "sample container retrieving commands" still cannot be determined, the "sample container retrieving command" targeting the sample container with the small number of the holding position is prioritized. FIG. 11G shows the command list CL of after the "sample container retrieving commands" of the command list CL of FIG. 11F are sorted by such rule.

When the sample containers in the first measurement unit 2 and the second measurement unit 3 are returned to the sample rack L, and the operation states of the first measurement unit and the second measurement unit 3 are transitioned to the "sample container retrievable" at the relevant time point, the "sample container retrieving command (6)" targeting on the sample container of the holding position 6 having the highest priority is executed. The sample container of the holding position 6 is transported to the second measurement unit 3 since only the second measurement unit 3 can measure the measurement item (CBC+DIFF item, RET, and NRBC) of the sample contained in the sample container of the holding position 6. When the "sample container retrieving command (6)" is executed, the "sample container retrieving command (6)" is deleted from the command list CL.

The execution determination process of the "sample container retrieving command (7)" targeting on the sample container of the holding position 7 having the highest priority is then carried out. Only the second measurement unit 3 can measure the measurement item (CBC+DIFF item, RET, and NRBC) of the sample contained in the sample container of the holding position 7, but the second measurement unit 3 is in the state of "sample container not retrievable/returnable" at this time point. Thus, the "sample container retrieving command (7)" is determined as not executable, and the execution determination process of the "sample container retrieving command (8)" targeting on the sample container of the holding position 8 having the next highest priority is carried out.

Since the measurement item (CBC+DIFF item, RET, and NRBC) of the sample in the sample containers of the holding positions 8 to 10 can be measured only by the second measurement unit 3, the "sample container retrieving command (8)", the "sample container retrieving command (9)", and the "sample container retrieving command (10)" are determined as not executable, similar to the above.

The execution determination process of the "sample container retrieving command (3)" targeting on the sample container of the holding position 3 having the next highest priority is then carried out. Since the first measurement unit 2 that can measure the measurement item (CBC+DIFF item) of the sample accommodated in the sample container of the holding position 3 is in the state of "sample container retrievable", the "sample container retrieving command (3)" is executed, and the sample container of the holding position 3 is transported to the first measurement unit 2. When the "sample container retrieving command (3)" is executed, the "sample container retrieving command (3)" is deleted from the command list CL.

The sample containers of the holding position 6 and the holding position 3 are returned to the sample rack L, the operation states of the first measurement unit and the second measurement unit 3 are transitioned to the "sample container retrievable", and thereafter, the processes similar to the above are repeated, so that the sample container of the holding position 7 is transported to the second measurement unit 3 and the sample container of the holding position 4 is transported to the first measurement unit 2. Since the "sample container retrieving command (7)" and the "sample container retrieving command (4)" are executed, the "sample container retrieving command (7)" and the "sample container retrieving command (4)" are deleted from the command list CL.

Similarly, the sample containers of the holding position 7 and the holding position 4 are returned to the sample rack L, and the operation states of the first measurement unit and the second measurement unit 3 are transitioned to the "sample container retrievable", and thereafter, the sample container of the holding position 8 is transported to the second measurement unit 3 and the sample container of the holding position 5 is transported to the first measurement unit 2. Since the "sample container retrieving command (8)" and the "sample container retrieving command (5)" are executed, the "sample container retrieving command (8)" and the "sample container retrieving command (5)" are deleted from the command list CL.

At this time point, the "sample container retrieving command (9)" and the "sample container retrieving command (10)" are remaining in the command list CL. The sample container of the holding position 8 is returned from the second measurement unit 3 to the sample rack L, and the operation state of the second measurement unit 3 is transitioned to the "sample container retrievable", and thereafter, the "sample container retrieving command (9)" is executed and the sample container of the holding position 9 is transported to the second measurement unit 3. Thereafter, the sample container of the holding position 9 is returned from the second measurement unit 3 to the sample rack L, and the operation state of the second measurement unit 3 is transitioned to the "sample container retrievable", and thereafter, the "sample container retrieving command (10)" is executed and the sample container of the holding position 10 is transported to the second measurement unit 3.

After all the sample containers T are returned, the sample rack L is sent from the rack transport path 43 to the post-analysis rack holding portion 42. Subsequently, the next sample rack L mounted on the pre-analysis rack holding portion 41 is sent from the pre-analysis rack holding portion 41 to the rack transport path 43, and the operations similar to the above are repeatedly carried out.

With the configuration described above, the first measurement unit 2 and the second measurement unit 3 are both effectively used, and the processing efficiency of the entire sample analyzer 1 can be enhanced.

Figure 12:
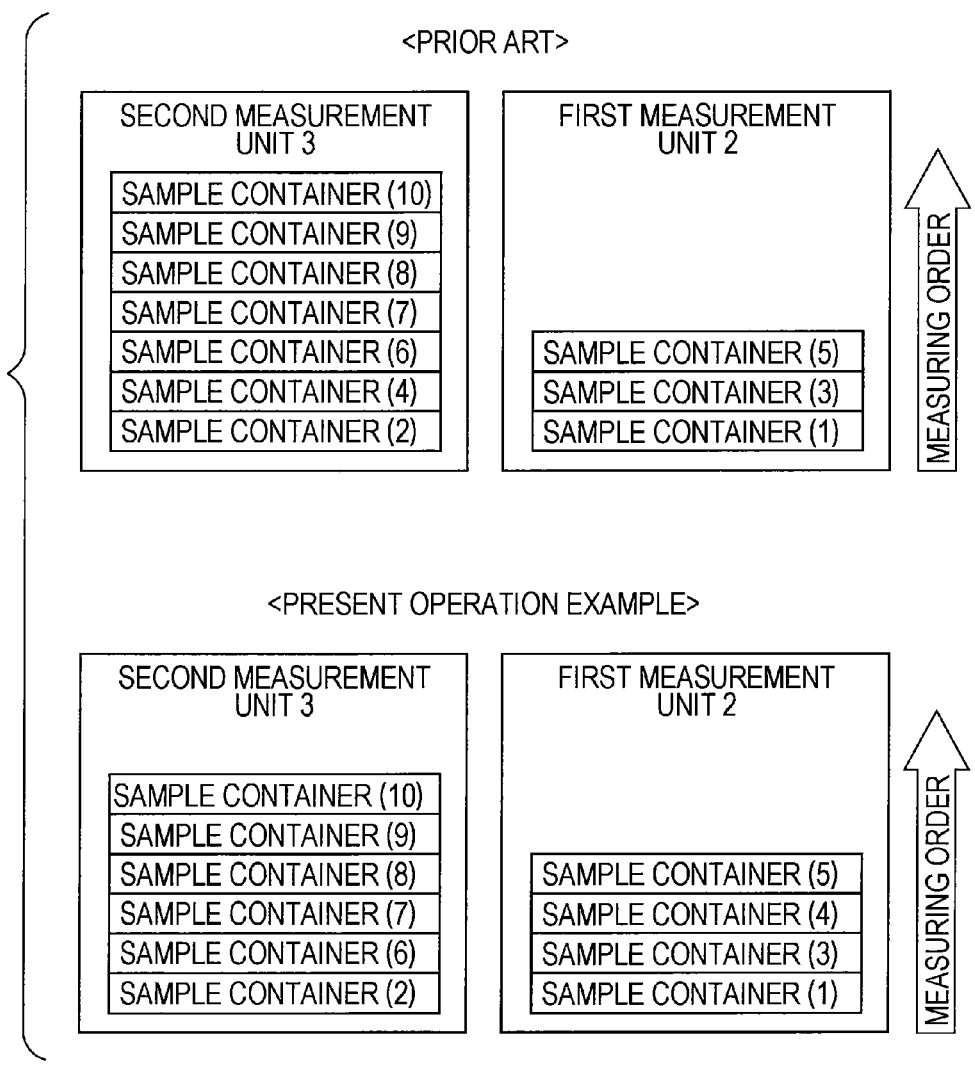
FIG. 12 is a schematic view showing the state of distribution of the sample container to the first measurement unit and the second measurement unit.

FIG. 12 is a schematic view in which a case where the sample containers in the sample rack are distributed to the first and second measurement units by the present operation example and a case where the sample containers in the sample rack are distributed to the first and second measurement units in order from the sample container positioned on the front side of the sample rack as in the prior art are compared. As shown in FIG. 12, in the conventional method, the first to the fifth sample containers are distributed to the first and second measurement units in order, but the sixth to the tenth sample containers are continuously transported only to the second measurement unit to perform the measurement. Thus, after the measurement of the fifth sample is terminated in the first measurement unit, the first measurement unit is not used at all for the measurement of the sample during the period until the measurement of the tenth sample is terminated in the second measurement unit. Therefore, both the first measurement unit and the second measurement unit are not effectively used, and the processing efficiency of the entire sample analyzer lowers.

According to the present operation example, on the other hand, after the first and second samples are transported to the first measurement unit and the second measurement unit, respectively, the measurement orders of the third to tenth samples are acquired, the sixth to tenth samples, for which the measurement orders include the RET and the NRBC, are preferentially transported to the second measurement unit, and the third to fifth samples, which measurement orders include only the CBC+DIFF item, are measured in the vacant first measurement unit. Therefore, as shown in FIG. 12, only three sample containers are distributed to the first measurement unit in the conventional method, whereas four sample containers can be distributed to the first measurement unit in the present operation example. Therefore, both the first measurement unit and the second measurement unit can be effectively used, and the processing efficiency of the entire sample analyzer can be enhanced.

According to the present embodiment, the sample container to be transported next and the transporting destination are determined based on the respective operation state data of the first measurement unit 2 and the second measurement unit 3, and hence the sample containers accommodated in the sample rack L can be more efficiently distributed according to the respective operation states of the first measurement unit 2 and the second measurement unit 3.

After the previous sample container is transported, the measurement order and the operation state data are monitored and the sample container to be transported next and the transporting destination thereof are determined in accordance therewith, and hence the sample container that can be efficiently transported and the transporting destination thereof can be appropriately determined based on the most recent measurement order and the operation state data.

When the first measurement unit 2 and the second measurement unit 3 perform the operation and are not in the "sample container retrievable" state, the sample information assigning operation that does not involve the operations of the first measurement unit 2 and the second measurement unit 3 is executed thereby enabling the sample process to be efficiently carried out.

The respective distance from the barcode reading position 43d to the first sample supply position 43a and the second sample supply position 43b can be reduced since the barcode reading position 43d is provided between the first sample supply position 43a and the second sample supply position 43b. Therefore, the sample container can be efficiently transported to the transporting destination after reading the sample barcode and acquiring the measurement order regardless of whether the transporting destination is the first measurement unit 2 or the second measurement unit 3.

Furthermore, the barcode reading portion of a complex configuration in which the sample barcodes of a plurality of sample containers T can be read simultaneously is not required since the sample barcode reading of each sample container is sequentially carried out.

Other Embodiments

The embodiments described above describe the configuration in which the sample rack can be transported one at a time on the rack transport path 43, but this is not the sole case. The configuration in which two sample racks can be simultaneously transported on the rack transport path 43 and the sample containers held in each sample rack are transported to the first measurement unit 2 and the second measurement unit 3 may be adopted.

In the embodiment described above, the barcode reading position 43d is provided between the first sample supply position 43a and the second sample supply position 43b, but the barcode reading position may be provided outside the region between the first sample supply position and the second sample supply position.

In the embodiment described above, the configuration in which the first measurement unit 2 and the second measurement unit 3 respectively take in the sample container T inside the unit, and the sample is aspirated from the sample container T inside the unit has been described, but this is not the sole case. A configuration in which the first measurement unit directly aspirates the sample from the sample container T at the first sample supply position, or a configuration in which the second measurement unit directly aspirates the sample from the sample container T at the second sample supply position may be adopted.

In the embodiment described above, a configuration in which the sample analyzer 1 includes two measurement units, the first measurement unit 2 and the second measurement unit 3, has been described, but this is not the sole case. The sample analyzer may include three or more measurement units, where after the transporting operation of one of the plurality of sample containers T held in the sample rack L is carried out, the sample container to be transported next may be selected based on the measurement order and the operation state data, and the relevant sample container may be transported to one of the three or more measurement units.

In the embodiment described above, an example in which the present invention is applied to a multi-item blood cell analyzer has been described, but this is not the sole case. The present invention may be applied to a sample analyzer other than the multi-item blood cell analyzer such as a blood coagulation measurement device, an immune analyzer, a urine formed element analyzer, or a urine qualitative analyzer.

In the embodiment described above, a configuration in which all the processes of the computer program 54a are executed by a single computer 5a has been described, but this is not the sole case, and a distributed system in which the processes similar to the computer program 54a are distributed and executed by a plurality of devices (computers) may be adopted.

In the embodiment described above, the configuration in which the sample is transported by the sample transport unit 4 to two measurement units 2, 3 arranged in a single sample analyzer 1 has been described, but this is not the sole case. The present invention may be applied to a sample analyzing system in which a plurality of independent measurement devices respectively including a sample transport unit are arranged, and the sample transport units are connected to form one transport line so that the sample rack can be transported to each measurement device along the transport line. In other words, after the transporting operation of one of the plurality of sample containers T held in the sample rack L is carried out, the sample container to be transported next is selected based on the measurement order and the operation state data, and the relevant sample container is transported to one of the plurality of measurement devices.

In the embodiment described above, the samples including only the CBC+DIFF item in the measurement order are held at the holding positions 1 and 2 of the sample rack L, and the sample ID and the measurement order corresponding to the samples at the holding positions 3 to 10 of the sample rack L are acquired by the CPU 51*a* while the first measurement unit 2 and the second measurement unit 3 are measuring such samples at the holding positions 1 and 2, but the present invention is not limited thereto. For instance, if the samples including the CBC+DIFF item, the RET, and the NRBC are held in the measurement order at each holding position 1 to 3 of the sample rack L, and the sample including only the CBC+DIFF item is held in the measurement order at the holding position 4, the CPU 51*a* may execute the following processes. First, both the first measurement unit 2 and the second measurement unit 3 are in the sample container retrievable state at the start of transportation of the sample rack, and hence the sample container is transported to the second measurement unit 3 after acquiring the sample ID and the measurement order corresponding to the sample at the holding position 1. The sample ID and the measurement order corresponding to the sample at the holding position 2 are then acquired. The sample ID and the measurement order corresponding to the sample at the holding position 3 are acquired since the second measurement unit 3 that can measure the sample is in the middle of the measuring operation. Since the second measurement unit 3 that can measure the sample is still in the middle of the measuring operation, the sample ID and the measurement order corresponding to the sample at the holding position 4 are acquired. The first measurement unit 2 capable of measuring the sample held at the holding position 4 is in the sample container retrievable state, and hence the relevant sample container is transported to the first measurement unit 2. While the first measurement unit 2 and the second measurement unit 3 are performing the measurement operation, the measurement orders of the samples accommodated in the remaining sample containers at the holding positions 5 to 10 are acquired. The time the first measurement unit 2 and the second measurement unit 3 are not measuring the sample is thus reduced and the sample processing performance of the sample analyzer 1 is enhanced through such processes.

The sample may start to be transported to each measurement unit after the sample IDs and the measurement orders corresponding to all the samples held in the sample rack L are acquired in advance.

What is claimed is:

1. A sample analyzer comprising:
   a first measurement unit configured to measure a sample accommodated in a sample container;
   a second measurement unit configured to measure a sample accommodated in a sample container;
   a rack transport unit configured to transport each of a plurality of sample containers held in a sample rack to either the first or the second measurement unit, wherein the rack transport unit is configured to transport the sample rack on a transport path in a first direction from the first measurement unit to the second measurement unit when transporting a first sample container held in the sample rack to the second measurement unit, and while the first sample container is processed, to transport the sample rack backwards on the transport path in a second direction from the second measurement unit to the first measurement unit when transporting a second sample container held in the sample rack to the first measurement unit; and
   a controller configured to:
   acquire a measurement item information indicating a measurement item of each of samples accommodated in the plurality of sample containers held in the sample rack;
   determine a sample container to be a transport object by determining priorities of transportation of the plurality of sample containers held in the sample rack based on the acquired plurality of measurement item information;
   determine a measurement unit to be a transport destination of the sample container determined as the transport object; and
   control the rack transport unit to transport the sample container determined as the transport object to the measurement unit determined as the transport destination,
   wherein the controller determines a priority of transportation of a sample container accommodating a sample measurable by only one of the first and second measurement units higher than a priority of transportation of a sample container accommodating a sample measurable by both of the first and second measurement units.

2. The sample analyzer of claim 1, wherein the controller acquires operation state information indicating an operation state of each of the first and second measurement units, and determines the transport object based on the acquired operation state information and the plurality of measurement item information.

3. The sample analyzer of claim 2, wherein the controller acquires the operation state information after a sample container has been transported to either the first or second measurement unit, and determines a sample container to be a next transport object based on the acquired operation state information and the plurality of measurement item information.

4. The sample analyzer of claim 2, wherein
   the operation state information of the first measurement unit is information indicating whether or not the first measurement unit is ready to take in a sample from a sample container; and
   the operation state information of the second measurement unit is information indicating whether or not the second measurement unit is ready to take in a sample from a sample container.

5. The sample analyzer of claim 1, wherein the rack transport unit includes:
   a setting portion where a sample rack is set by a user; and
   a storage portion configured to store the sample rack transported from the transport path, wherein
   the controller determines a priority of transportation of a sample container positioned on the storage portion side on the transport path higher than a priority of transportation of a sample container positioned on the setting portion side.

6. The sample analyzer of claim 1, wherein the controller acquires operation state information indicating an operation state of each of the first and second measurement units,
   determines whether at least one of the first and second measurement units can measure a sample accommodated in a sample container having a first priority based on the acquired operation state information, determines the sample container having the first priority as the transport object when at least one of the first and second measurement units can measure the sample accommodated in the sample container having the first priority, and when the first and second measurement units cannot measure the sample accommodated in the sample container having the first priority, determines whether or not at least one of the first and second measurement units can measure a sample accommodated in a sample container having a second priority which is a next highest priority after the first priority.

7. The sample analyzer of claim 2, wherein the controller determines the transport destination based on a single measurement item information of a sample accommodated in the sample container determined as the transport object and the operation state information.

8. The sample analyzer of claim 7, wherein the controller determines a measurement unit with lesser number of measurable measurement items of the first and second measurement units as the transport destination when both of the first and second measurement units can measure the sample accommodated in the sample container determined as the transport object.

9. The sample analyzer of claim 8, wherein the controller calculates a difference between a number of measurement items of the sample accommodated in the sample container determined as the transport object and each of a number of measurement items measurable by the first measurement unit and a number of measurement items measurable by the second measurement unit, and determines the transport destination based on the calculated difference when both of the first and second measurement units can measure the sample accommodated in the sample container determined as the transport object.

10. The sample analyzer of claim 7, wherein the rack transport unit includes a storage portion configured to store the sample rack transported from the transport path, wherein the controller determines a measurement unit on the storage portion side of the first and second measurement units as the transport destination when both of the first and second measurement units can measure the sample accommodated in the sample container determined as the transport object.

11. The sample analyzer of claim 1, wherein when both of the first and second measurement units is ready to take in a sample from a sample container, the controller acquires measurement item information of a first sample accommodated in a first sample container held at a head of the sample rack, controls the rack transport unit to transport the first sample container to either one of the first or second measurement unit based on the measurement item information, determines a second sample container accommodating a second sample measurable by the other measurement unit by acquiring measurement item information of samples sequentially from a sample container held at a position next to the first sample container in the sample rack, controls the rack transport unit to transport the determined second sample container to the other measurement unit, and acquires measurement item information of each of samples accommodated in a plurality of remaining sample containers held in the sample rack while the first and second measurement units are measuring the first and second samples.

12. The sample analyzer of claim 1, wherein each of the first and second measurement unit is configured to measure a clinical sample.

13. A sample transporting method for transporting each of a plurality of sample containers held in a sample rack to either a first measurement unit or a second measurement unit by a rack transport unit, wherein the rack transport unit is configured to transport the sample rack on a transport path in a first direction from the first measurement unit to the second measurement unit when transporting a first sample container held in the sample rack to the second measurement unit, and while the first sample container is processed, to transport the sample rack backwards on the transport path in a second direction from the second measurement unit to the first measurement unit when transporting a second sample container held in the sample rack to the first measurement unit;

the method comprising:

acquiring a measurement item information indicating a measurement item of each of samples accommodated in the plurality of sample containers held in the sample rack;

determining a sample container to be a transport object from the plurality of sample containers by determining priorities of transportation of the plurality of sample containers based on the acquired plurality of measurement item information;

determining a measurement unit to be a transport destination of the sample container determined as the transporting object from the first and second measurement units; and transporting the sample container determined as the transport object to the measurement unit determined as the transport destination by the rack transport unit, wherein a priority of transportation of a sample container accommodating a sample measurable by only one of the first and second measurement units is determined higher than a priority of transportation of a sample container accommodating a sample measurable by both of the first and second measurement units.

14. The sample transporting method of claim 13, further comprising acquiring operation state information indicating an operation state of each of the first and second measurement units, wherein the transport object is determined based on the acquired operation state information and the plurality of measurement item information.

15. The sample transporting method of claim 14, wherein the transport destination is determined based on a single measurement item information of a sample accommodated in the sample container determined as the transport object and the operation state information.

16. The sample transporting method of claim 15, wherein a measurement unit with lesser number of measurable measurement items of the first and second measurement units is determined as the transport destination when both of the first and second measurement units can measure the sample accommodated in the sample container determined as the transport object.

17. A sample analyzer comprising:

a first measurement unit configured to measure a sample accommodated in a sample container;

a second measurement unit configured to measure a sample accommodated in a sample container;

a rack transport unit configured to transport each of a plurality of sample containers held in a sample rack to either the first or the second measurement unit, wherein the rack transport unit is configured to transport the sample rack on a transport path in a first direction from the first measurement unit to the second measurement unit when transporting a first sample container held in the sample rack to the second measurement unit, and while the first sample container is processed, to transport the sample rack backwards on the transport path in a second direction from the second measurement unit to the first measurement unit when transporting a second sample container held in the sample rack to the first measurement unit; and a controller configured to:

acquire a measurement item information indicating a measurement item of each of samples accommodated in the plurality of sample containers held in the sample rack;

determine a sample container to be a transport object;

when both of the first and second measurement units can measure the sample accommodated in the sample container determined as the transport object, obtain a difference between a number of measurement items of the sample accommodated in the transport object and each of a number of measurement items measurable by the first measurement unit and a number of measurement items measurable by the second measurement unit, and determine a measurement unit with less difference to be a transport destination of the transport object; and control the rack transport unit to transport the sample container determined as the transport object to the measurement unit determined as the transport destination, wherein the rack transport unit includes a storage portion configured to store the sample rack transported from the transport path, and the controller is configured to determine a measurement unit on the storage portion side of the first and second measurement units as the transport destination when the difference is equal between the first and the second measurement units.

* * * * *